US012703694B2

(12) United States Patent
Ying et al.

(10) Patent No.: US 12,703,694 B2
(45) Date of Patent: Aug. 11, 2026

(54) PYRAZOLE CARBOXYLATE ESTER COMPOUND AND USE THEREOF

(71) Applicants: SHENYANG SINOCHEM AGROCHEMICALS R&D CO., LTD., Shenyang (CN); JIANGSU YANGNONG CHEMICAL CO., LTD., Yangzhou (CN)

(72) Inventors: Junwu Ying, Shenyang (CN); Huibin Yang, Shenyang (CN); Hongjuan Ma, Shenyang (CN); Bo Qin, Shenyang (CN); Dongliang Cui, Shenyang (CN); Mingxin Wang, Shenyang (CN); Gang Wang, Shenyang (CN); Bing Sun, Shenyang (CN); Fan Zhang, Shenyang (CN); Lin Chen, Shenyang (CN); Shuang Liang, Shenyang (CN); Bin Li, Shenyang (CN)

(73) Assignees: SHENYANG SINOCHEM AGROCHEMICALS R&D CO., LTD., Shenyang (CN); JIANGSU YANGNONG CHEMICAL CO., LTD., Yangzhou (CN)

( * ) Notice: Subject to any disclaimer, the term of this patent is extended or adjusted under 35 U.S.C. 154(b) by 942 days.

(21) Appl. No.: 17/905,791

(22) PCT Filed: Mar. 12, 2021

(86) PCT No.: PCT/CN2021/080370

§ 371 (c)(1),
(2) Date: Sep. 7, 2022

(87) PCT Pub. No.: WO2021/180193

PCT Pub. Date: Sep. 16, 2021

(65) Prior Publication Data

US 2023/0138225 A1 May 4, 2023

(30) Foreign Application Priority Data

Mar. 13, 2020 (CN) ......................... 202010174413.7

(51) Int. Cl.

| | |
|---|---|
| ***C07D 403/12*** | (2006.01) |
| ***A01N 43/56*** | (2006.01) |
| ***A01P 13/00*** | (2006.01) |

(52) U.S. Cl.

CPC ........... *C07D 403/12* (2013.01); *A01N 43/56* (2013.01); *A01P 13/00* (2021.08)

(58) Field of Classification Search

CPC .................................................... C07D 403/12

See application file for complete search history.

(56) References Cited

U.S. PATENT DOCUMENTS 6,156,702 A 12/2000 Engel et al.

FOREIGN PATENT DOCUMENTS

| | | | |
|---|---|---|---|
| CN | 86101277 | A | 11/1986 |
| CN | 101298451 | A | 11/2008 |
| CN | 101573035 | A | 11/2009 |
| CN | 107674025 | A | 2/2018 |
| CN | 110903279 | A | 3/2020 |
| EP | 0240001 | A1 | 10/1987 |
| WO | 2017113509 | A1 | 7/2017 |

OTHER PUBLICATIONS

English translated description of CN 110903279, 2020.*

* cited by examiner

*Primary Examiner* — Brian E Mcdowell

(74) *Attorney, Agent, or Firm* — NKL Law; Allen Xue

(57) ABSTRACT

Pyrazole carboxylate ester compounds have a structural formula of formula (I):

I

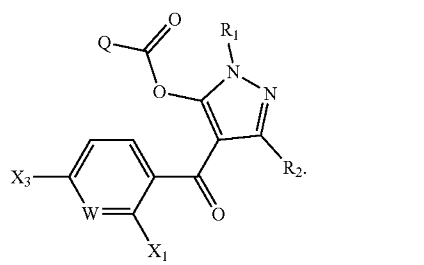

Q is $Q_1$ or $Q_3$ $Q_1$

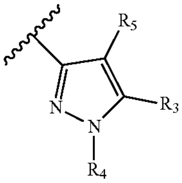

$Q_3$

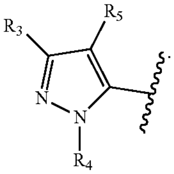

The pyrazole carboxylate ester compounds has herbicidal activity and can be used for controlling weeds.

6 Claims, No Drawings

PYRAZOLE CARBOXYLATE ESTER COMPOUND AND USE THEREOF

TECHNICAL FIELD

The present invention relates to herbicide, and specifically to a kind of pyrazole carboxylate ester compounds and the uses thereof.

BACKGROUND

Due to the succession and change of weed populations and the emergence and rapid development of resistance to chemical pesticides, people have continuously strengthened awareness on ecological environmental protection, and have paid more attention to the knowledge of chemical pesticide pollution and the influence of pesticides on non-target organisms and the end-result problem in the pesticide ecological environment. With the gradual decrease of the arable land area in the world, the continuous increase of the population and the increase of the demands for food, people are forced to rapidly develop agricultural production technologies, enhance and improve the farming system, and continuously invent novel and improved herbicidal compounds and compositions.

CN107674025A has reported that some pyrazole carboxylate ester compounds have herbicidal activity, such as compound 144 (KC1) and compound 143 (KC2):

KC1

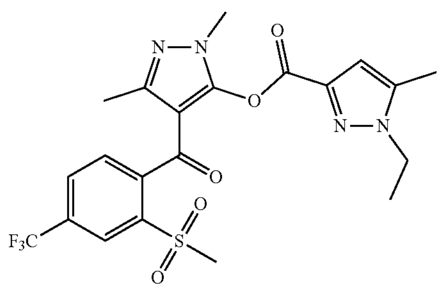

KC2

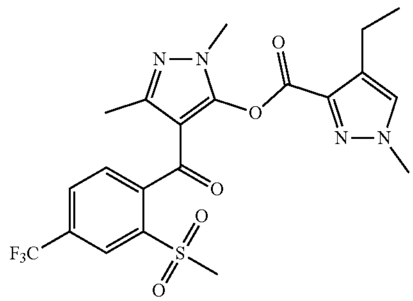

WO2017113509A1 has reported that a kind of pyrazole carboxylate ester compounds have herbicidal activity. One of the compounds has been subsequently developed and commercialized with the ISO common name fenpyrazone and the structural formula as follows:

KC3

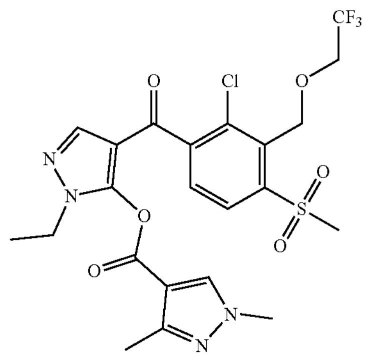

The pyrazole carboxylate ester compounds shown in the present invention are not disclosed.

SUMMARY

The purpose of the present invention is to provide a kind of pyrazole carboxylate ester compounds with novel structure and safety for crops and the uses thereof.

To achieve the above purpose, the present invention adopts the following technical solution:

A kind of pyrazole carboxylate ester compounds are provided, as shown in the general formula I:

I

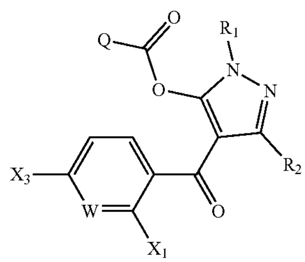

Wherein:

$X_1$ is selected from methyl or chlorine;

W is selected from $CX_2$;

$X_2$ is selected from $Y_1$ oxy;

$Y_1$ is selected from $C_1$-$C_6$ alkyl, $C_1$-$C_6$ haloalkyl, $C_3$-$C_6$ cycloalkyl, $C_3$-$C_6$ cycloalkyl $C_1$-$C_6$ alkyl, $C_1$-$C_6$ alkoxy $C_1$-$C_6$ alkyl, $C_2$-$C_6$ alkenyl, $C_2$-$C_6$ alkynyl, phenyl, 5-7 membered aliphatic heterocycle containing 1-4 heteroatoms, 5-7 membered aromatic heterocycle containing 1-4 heteroatoms, 5-7 membered aliphatic heterocyclic $C_1$-$C_6$ alkyl containing 1-4 heteroatoms or 5-7 membered aromatic heterocyclic $C_1$-$C_6$ alkyl containing 1-4 heteroatoms; the hydrogen on the phenyl, the aliphatic heterocycle and the aromatic heterocycle mentioned above can be substituted by one or more of the following substituents which are selected from nitro, halogen, $C_1$-$C_6$ alkyl, $C_1$-$C_6$ haloalkyl, $C_1$-$C_6$ alkoxy, $C_1$-$C_6$ haloalkoxy, $C_3$-$C_6$ cycloalkyl, $C_3$-$C_6$ cycloalkoxy, $C_2$-$C_6$ alkenyl, $C_2$-$C_6$ alkynyl, phenyl or halophenyl;

$X_3$ is selected from methylsulfonyl;

Q is selected from $Q_1$ or $Q_3$;

$Q_1$

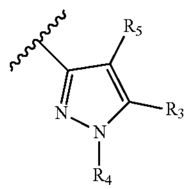

$Q_3$

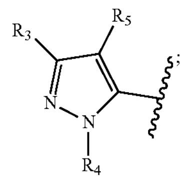

$R_1$ is selected from $C_1$-$C_6$ alkyl, $C_1$-$C_6$ haloalkyl, $C_3$-$C_6$ cycloalkyl, $C_3$-$C_6$ halocycloalkyl, $C_3$-$C_6$ cycloalkyl $C_1$-$C_3$ alkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkylsulfonyl, $C_1$-$C_6$ haloalkylsulfonyl, $C_1$-$C_6$ alkoxy $C_1$-$C_3$ alkyl, $C_1$-$C_6$ haloalkoxy $C_1$-$C_3$ alkyl or $C_1$-$C_6$ alkoxy $C_1$-$C_3$ alkoxy $C_1$-$C_3$ alkyl;

$R_2$ and $R_3$ can be the same or different, and are respectively selected from hydrogen, $C_1$-$C_6$ alkyl, $C_1$-$C_6$ haloalkyl, $C_3$-$C_6$ cycloalkyl, $C_3$-$C_6$ halocycloalkyl, $C_3$-$C_6$ cycloalkyl $C_1$-$C_6$ alkyl, $C_3$-$C_6$ halocycloalkyl $C_1$-$C_3$ alkyl, $C_1$-$C_6$ alkoxy, $C_2$-$C_6$ alkenyl or $C_2$-$C_6$ alkynyl;

$R_4$ is selected from ethyl;

$R_5$ is selected from hydrogen, halogen, $C_1$-$C_6$ alkyl or $C_1$-$C_6$ haloalkyl.

The preferred compounds of general formula I of this invention are:

$X_1$ is selected from methyl or chlorine;

W is selected from $CX_2$;

$X_2$ is selected from $Y_1$ oxy;

$Y_1$ is selected from $C_1$-$C_6$ alkyl, $C_1$-$C_6$ haloalkyl, $C_1$-$C_6$ alkoxy $C_1$-$C_6$ alkyl, $C_3$-$C_6$ cycloalkyl, $C_3$-$C_6$ cycloalkyl $C_1$-$C_6$ alkyl, $C_2$-$C_6$ alkenyl or $C_2$-$C_6$ alkynyl;

$X_3$ is selected from methylsulfonyl;

Q is selected from $Q_1$ or $Q_3$;

$Q_1$

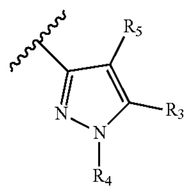

$Q_3$

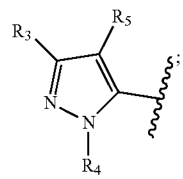

$R_1$ is selected from $C_1$-$C_6$ alkyl, $C_1$-$C_6$ haloalkyl, $C_3$-$C_6$ cycloalkyl, $C_3$-$C_6$ halocycloalkyl, $C_3$-$C_6$ cycloalkyl $C_1$-$C_3$ alkyl, $C_2$-$C_6$ alkenyl, $C_2$-$C_6$ alkynyl or $C_1$-$C_6$ alkoxy $C_1$-$C_3$ alkyl;

$R_2$ and $R_3$ can be the same or different, and are respectively selected from hydrogen, $C_1$-$C_6$ alkyl, $C_1$-$C_6$ haloalkyl, $C_3$-$C_6$ cycloalkyl or $C_3$-$C_6$ halocycloalkyl, $C_3$-$C_6$ cycloalkyl $C_1$-$C_6$ alkyl, $C_3$-$C_6$ halocycloalkyl $C_1$-$C_3$ alkyl, $C_1$-$C_6$ alkoxy, $C_2$-$C_6$ alkenyl or $C_2$-$C_6$ alkynyl;

$R_4$ is selected from ethyl;

$R_5$ is selected from hydrogen, halogen or $C_1$-$C_6$ alkyl.

Furthermore, the preferred compounds of general formula I of this invention are:

$X_1$ is selected from methyl or chlorine;

W is selected from $CX_2$;

$X_2$ is selected from $Y_1$ oxy;

$Y_1$ is selected from $C_1$-$C_6$ alkyl, $C_1$-$C_6$ haloalkyl, $C_3$-$C_6$ cycloalkyl, $C_3$-$C_6$ cycloalkyl $C_1$-$C_6$ alkyl or $C_1$-$C_6$ alkoxy $C_1$-$C_6$ alkyl;

$X_3$ is selected from methylsulfonyl;

Q is selected from $Q_1$ or $Q_3$;

$Q_1$

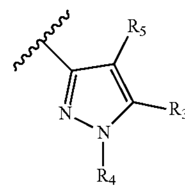

$Q_3$

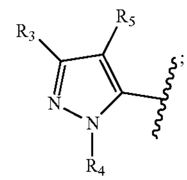

$R_1$ is selected from $C_1$-$C_6$ alkyl, $C_1$-$C_6$ haloalkyl, $C_3$-$C_6$ cycloalkyl $C_1$-$C_3$ alkyl or $C_1$-$C_6$ alkoxy $C_1$-$C_3$ alkyl;

$R_2$ and $R_3$ can be the same or different, and are respectively selected from hydrogen, $C_1$-$C_6$ alkyl, $C_1$-$C_6$ haloalkyl, $C_3$-$C_6$ cycloalkyl or $C_3$-$C_6$ cycloalkyl $C_1$-$C_6$ alkyl;

$R_4$ is selected from ethyl;

$R_5$ is selected from hydrogen.

Even more preferred compounds of general formula I of this invention are:

$X_1$ is selected from methyl or chlorine;

W is selected from $CX_2$;

$X_2$ is selected from $Y_1$ oxy;

$Y_1$ is selected from $C_1$-$C_6$ alkyl, $C_3$-$C_6$ cycloalkyl $C_1$-$C_6$ alkyl or $C_1$-$C_6$ alkoxy $C_1$-$C_6$ alkyl;

$X_3$ is selected from methylsulfonyl;

Q is selected from $Q_1$ or $Q_3$;

$Q_1$

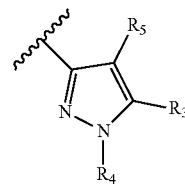

-continued

Q3

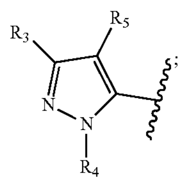

$R_1$ is selected from $C_1$-$C_6$ alkyl;

$R_2$ and $R_3$ can be the same or different, and are respectively selected from hydrogen, $C_1$-$C_6$ alkyl or $C_3$-$C_6$ cycloalkyl;

$R_4$ is selected from ethyl;

$R_5$ is selected from hydrogen.

In the definitions of the compounds of the formula I provided above, the terms used in the collection are defined as follows:

Alkyl refers to linear or branched groups such as methyl, ethyl, n-propyl, isopropyl, n-butyl, isobutyl, sec-butyl, tert-butyl, n-pentyl, isopentyl and n-hexyl. Cycloalkyl refers to groups in the form of cyclic chain, such as cyclopropyl, methylcyclopropyl, cyclopropylcyclopropyl, cyclobutyl, cyclopentyl and cyclohexyl. Alkenyl refers to linear or branched alkenyl, such as 1-propenyl, 2-propenyl, butenyl, pentenyl and hexenyl. Alkynyl refers to linear or branched chain alkynyl, such as 1-propynyl, 2-propynyl, butynyl, pentynyl and hexynyl. Alkoxy refers to a group having an oxygen atom at the end of the alkyl, such as methoxy, ethoxy, n-propoxy, isopropoxy and tert-butoxy. The 5-7-membered heterocycle containing 1-4 heteroatoms refers to a 5-7-membered heterocyclic compound containing 1-4 heteroatoms without aromatic characteristics, such as ethylene oxide, tetrahydrofuran, imidazolinone and caprolactam. The 5-7-membered aromatic heterocycle containing 1-4 heteroatoms refers to a 5-7-membered heterocyclic compound containing 1-4 heteroatoms having aromatic characteristics, such as furan, thiophene, pyrazole and pyridine.

The compounds having general formula I in the present invention can be prepared by the following method:

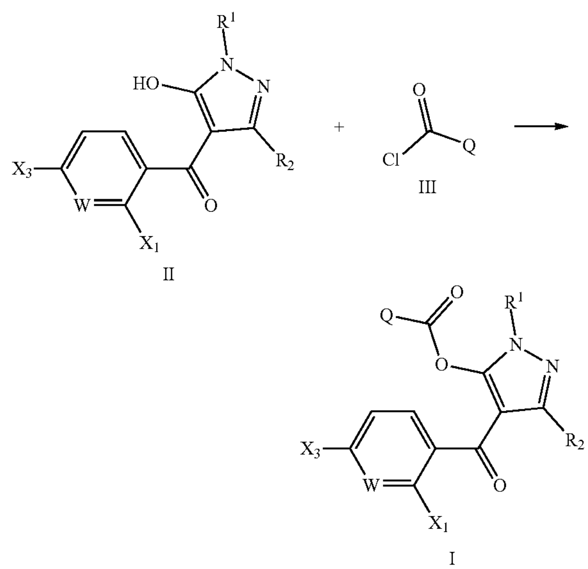

II III I

The compounds having general formula II and the compounds having general formula III react in a suitable solvent at temperature of −10° C. to a boiling point of the suitable solvent for 0.5-48 hours to obtain the target compounds I. The suitable solvent can be selected from dichloromethane, 1,2-dichloroethane, chloroform, carbon tetrachloride, hexane, benzene, toluene, ethyl acetate, acetonitrile, acetic acid, tetrahydrofuran, dioxane, N,N-dimethylformamide or dimethylsulfoxide.

Addition of a suitable alkali substance can be beneficial to the reaction. The suitable alkali can be selected from organic alkali such as triethylamine, N, N-dimethylaniline or pyridine, or inorganic alkali such as sodium hydroxide, potassium hydroxide, sodium carbonate, sodium bicarbonate, potassium carbonate, sodium methoxide, sodium tert-butoxide or potassium tert-butoxide.

The preparation method of the compounds of the general formula II is as follows:

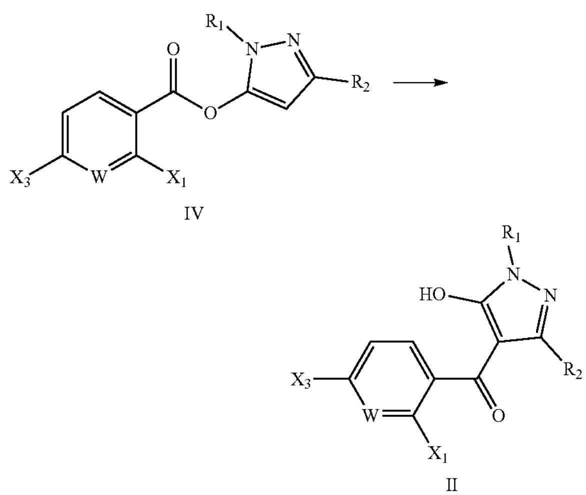

IV II

The compounds having general formula IV react under the action of proper alkali and proper catalyst in a suitable solvent at temperature of −10° C. to a boiling point of the suitable solvent for 0.5-48 hours to obtain the compounds having general formula II. The suitable solvent mentioned above can be selected from dichloromethane, 1,2-dichloroethane, chloroform, carbon tetrachloride, hexane, benzene, toluene, ethyl acetate, acetonitrile, acetic acid, tetrahydrofuran, dioxane, N,N-dimethylformamide or dimethylsulfoxide. The proper alkali mentioned above can be selected from sodium carbonate, potassium carbonate or triethylamine. The proper catalyst mentioned above can be selected from sodium carbonate, potassium carbonate, acetone cyanohydrin, azide, azide quaternary ammonium salt, metal cyanide or DMAP.

The preparation method of the compounds of the formula IV is as follows:

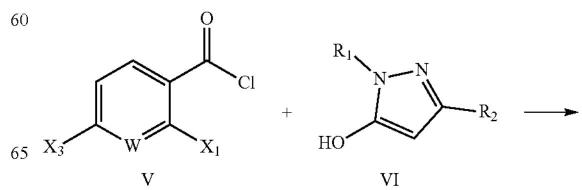

V VI

-continued

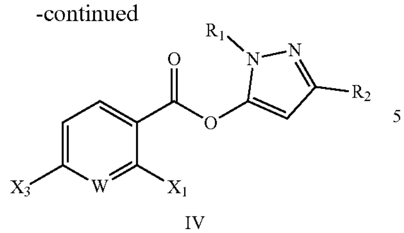

IV

The compounds having general formula V and the compounds having general formula VI (commercially available or prepared by the method described in reference EP0240001) react in a suitable solvent at temperature of −10° C. to a boiling point of the suitable solvent for 0.5-24 hours to obtain the compounds having general formula IV. The suitable solvent mentioned above can be selected from dichloromethane, 1,2-dichloroethane, chloroform, carbon tetrachloride, hexane, benzene, toluene, ethyl acetate, acetonitrile, acetic acid, tetrahydrofuran, dioxane, N,N-dimethylformamide or dimethylsulfoxide.

Addition of a suitable alkali substance can be beneficial to the reaction. The suitable alkali can be selected from organic alkali such as triethylamine, N, N-dimethylaniline or pyridine, or inorganic alkali such as sodium hydroxide, potassium hydroxide, sodium carbonate, sodium bicarbonate, potassium carbonate, sodium methoxide, sodium tert-butoxide or potassium tert-butoxide.

The corresponding raw material carboxylic acid (commercially available or prepared by the method described in reference CN86101277A or CN101573035A) of the compounds having general formula V and an acyl halide reagent react in a suitable solvent at temperature of −10° C. to a boiling point of the suitable solvent for 0.5-48 hours to obtain the compounds having general formula V. The acyl halide reagent can be selected from oxalyl chloride, thionyl chloride, phosphorous oxychloride, phosphorus trichloride or phosphorus pentachloride. The suitable solvent can be selected from dichloromethane, 1,2-dichloroethane, hexane, benzene, toluene, acetonitrile, acetic acid, dioxane or liquid acyl halide reagent.

The preparation method of the compounds having general formula III is as follows:

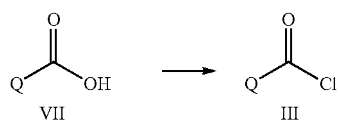

VII III

The compounds having general formula VII react with the acyl halide reagent in a suitable solvent at temperature of −10° C. to a boiling point of the suitable solvent for 0.5-48 hours to obtain the compounds having general formula III. The acyl halide reagent can be selected from oxalyl chloride, thionyl chloride, phosphorous oxychloride, phosphorus trichloride or phosphorus pentachloride. The suitable solvent can be selected from dichloromethane, 1,2-dichloroethane, hexane, benzene, toluene, acetonitrile, acetic acid, dioxane or liquid acyl halide reagent.

The preparation method of the compounds having general formula VII is as follows:

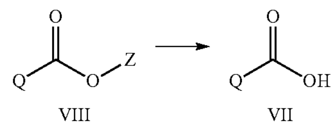

VIII VII

Z is selected from $C_1$-$C_4$ alkyl.

The compounds having general formula VIII react with the suitable alkali in a suitable solvent at temperature of −10° C. to a boiling point of the suitable solvent for 0.5-48 hours to obtain the compounds having general formula VII. The suitable alkali can be selected from sodium hydroxide or potassium hydroxide. The suitable solvent can be selected from methanol, ethanol, tetrahydrofuran, toluene, DMF, DMSO, acetonitrile or dioxane.

The preparation method of the compounds having general formula VIII is as follows:

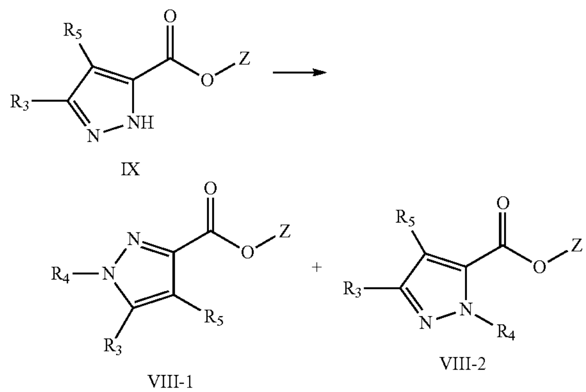

IX

VIII-1 VIII-2

Z is selected from $C_1$-$C_4$ alkyl.

The compounds having general formula IX react with a suitable ethylating reagent in a suitable solvent at temperature of −10° C. to a boiling point of the suitable solvent for 0.5-48 hours to obtain the compounds having general formula VIII. The suitable ethylating reagent can be selected from bromoethane, iodoethane or diethyl sulfate. The suitable solvent can be selected from methanol, ethanol, butanol, pentanol, tetrahydrofuran, toluene, ethyl acetate, butyl acetate, ethyl benzoate, anisole, methyl tert-butyl ether, DMF, DMSO, acetonitrile, dioxane or ethylating reagent.

The above reaction can be conducted under different conditions. In the reaction process, isomers may be produced, and addition of a suitable alkali is beneficial to generate the compounds having general formula VIII-1. The suitable alkali can be selected from triethylamine, N, N-dimethylaniline, pyridine, sodium hydroxide, sodium hydride, potassium hydroxide, sodium carbonate, sodium bicarbonate, potassium carbonate, sodium methoxide, sodium ethylate, sodium tert-butoxide or potassium tert-butoxide. Diethyl sulfate is used as the ethylating reagent, which is beneficial to generate the compounds having general formula VIII-2. The generated isomers can be separated by column chromatograph purification, distillation, recrystallization and other methods to get the compounds having general formula VIII-1 and VIII-2 respectively.

The compounds having general formula IX are commercially available or prepared by the method described in reference CN101298451A.

The compounds having general formula I of the present invention have herbicidal activity and can be used for controlling various weeds. Compared with the compounds disclosed in the prior art, the pyrazole carboxylate ester compounds of the present invention not only have excellent herbicidal activity, but also are safe for crops.

The present invention further comprises herbicidal compositions using the compounds having general formula I as active ingredient. The weight percentage of the active ingredient in the herbicidal composition is 1-99%. The herbicidal compositions further comprises agriculturally acceptable carriers.

The herbicidal compositions of the present invention can be applied in the forms of various formulations. The compounds of the present invention are generally dissolved or dispersed in the carrier and prepared into the formulations for easier dispersion when used as herbicide. For example, the chemical formulations can be prepared into wettable powder or missible oil. Therefore, in the compositions, at least one liquid or solid carrier is added, and generally a suitable surfactant needs to be added.

The present invention further provides an implementing method for controlling weeds. The method comprises applying an effective dose of the herbicidal composition of the present invention to the weed or a weed growing place or a surface of a growth medium thereof. A suitable effective dose is 1 to 1000 grams per hectare, and a preferred effective dose is 10 to 500 grams per hectare. For some applications, one or more other herbicides can be added to the herbicidal composition of the present invention, thereby generating additional advantages and effects.

The compounds of the present invention can be used alone or in combination with other known pesticides, bactericides, plant growth regulators or fertilizers.

It should be clear that various changes and modifications can be made within the scope defined by the claims of the present invention.

The present invention has the following advantages:

Compared with the known pyrazole carboxylate ester compounds, the compounds having general formula I in the present invention comprise a benzoyl and a pyrazolyl acyl substitution, which are novel in structure. The pyrazole carboxylate ester compounds in the present invention have unexpectedly high herbicidal activity, also have high herbicidal activity at a lower dosage, not only have high efficiency, but also reduce the use amount of pesticides, reduce the cost and reduce environmental pollution.

DETAILED DESCRIPTION

The following examples and biometric test results can be used to further illustrate the present invention, but are not intended to limit the present invention.

Preparation Example

Example 1 the Preparation of Compound 1-32

(1) The Preparation of 2-methyl-3-methoxyethoxy-4-methylsulfuryl Benzoyl Chloride

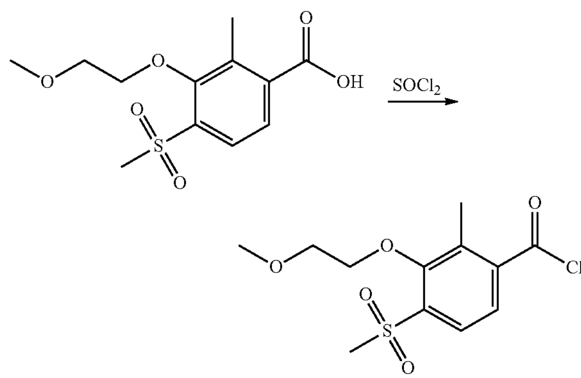

2-methyl-3-methoxyethoxy-4-methylsulfuryl benzoic acid (1.1 g, 3.8 mmol, prepared according to CN101573035A) and toluene (20 mL) were added to a reaction flask, thionyl chloride (2.4 g, 19.1 mmol) was slowly added. The mixture was heated and refluxed for 4 hours, and the solvent was evaporated under reduced pressure to obtain 1.2 g of yellow oil, which was directly used in the next step.

(2) The Preparation of 2-methyl-3-methoxyethoxy-4-methylsulfuryl benzoyl-1-ethyl-5-hydroxypyrazole Ester

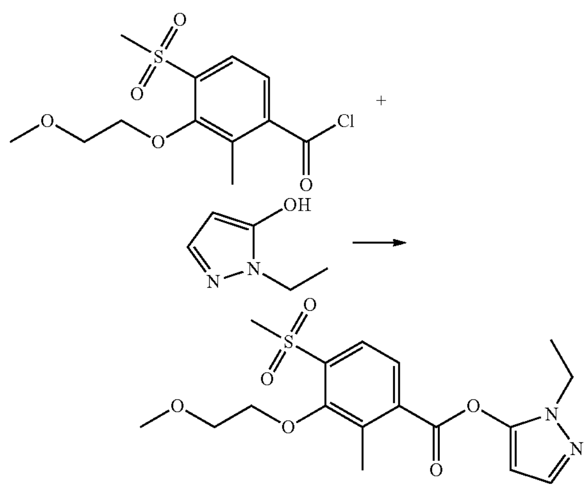

1-ethyl-5-hydroxypyrazole (0.43 g, 3.8 mmol), 1,2-dichloroethane (20 mL) and triethylamine (0.43 g, 4.2 mmol) were added to the reaction flask, and the 1,2-dichloroethane solution (10 mL) of 2-methyl-3-methoxyethoxy-4-methylsulfuryl benzoyl chloride in the above step was added dropwise. The mixture was stirred at room temperature for 2 hours. The organic phase was washed with water (20 ml)

and dried with anhydrous magnesium sulfate. The solvent was evaporated under reduced pressure, and the residue was separated by column chromatography to obtain 1.2 g of yellow oil with a yield of 80%.

$^1H$ NMR (600 MHz, $CDCl_3$): 7.95-7.99 (m, 2H), 7.49 (d, 1H), 6.25 (d, 1H), 4.25 (t, 2H), 4.11 (q, 2H), 3.83 (t, 2H), 3.49 (s, 3H), 3.32 (s, 3H), 2.66 (s, 3H), 1.45 (t, 3H).

(3) The Preparation of 4-(2-methyl-3-methoxyethoxy-4-methylsulfuryl benzoyl)-1-ethyl-5-hydroxypyrazole

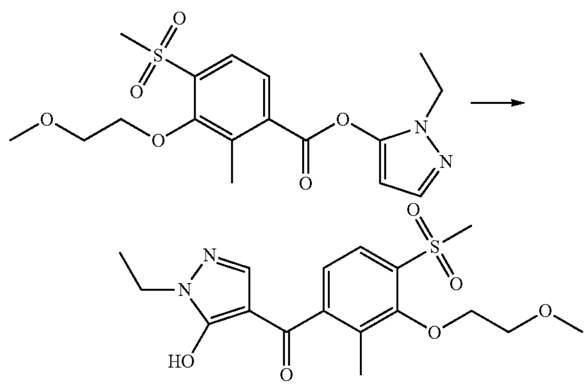

2-methyl-3-methoxyethoxy-4-methylsulfuryl benzoyl-1-ethyl-5-hydroxypyrazole ester (1.2 g, 3.1 mmol), 1, 2-dichloroethane (20 mL), triethylamine (0.48 g, 4.7 mmol) and 2 drops of acetone cyanohydrin were added to the reaction flask. The mixture was stirred overnight at room temperature. Water (50 mL) was added to stir for half an hour. The aqueous phase was adjusted with 10% dilute hydrochloric acid to pH=2-3, and extracted with ethyl acetate (50 mL*2) twice. The combined organic phase was washed with saturated salt water (50 mL) and dried with anhydrous magnesium sulfate, and the solvent was evaporated under reduced pressure to obtain 1.1 g of yellow oil with a yield of 91%.

(4) The Preparation of 1-ethyl-5-methyl-3-pyrazole Ethyl Formate

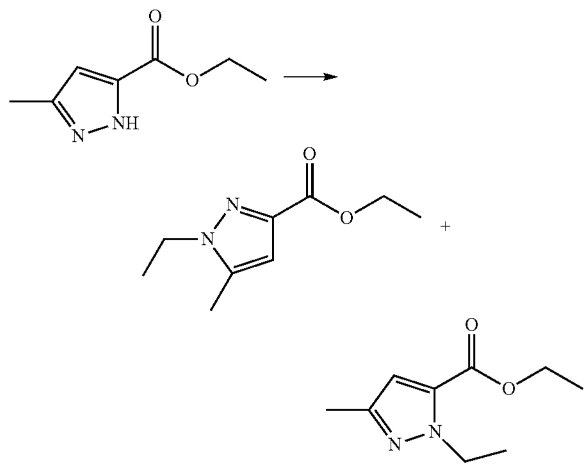

3-methyl-5-pyrazole ethyl formate (10 g, 64.9 mmol, prepared according to CN101298451A) was added to the reaction flask, diethyl sulfate (13 g, 84.4 mmol) was added slowly. The mixture was kept at 80-85° C. for 5 hours, and cooled to room temperature. Ethyl acetate (200 mL) and water (100 mL) were used for extraction. The organic phase was sequentially washed with saturated salt water (50 mL) and dried with anhydrous magnesium sulfate. The solvent was evaporated under reduced pressure, and the residue was separated by column chromatography to obtain 1.2 g of 1-ethyl-5-methyl-3-pyrazole ethyl formate, yellow oil, with a yield of 10% and obtain 9 g of 1-ethyl-3-methyl-5-pyrazole ethyl formate, colorless oil, with a yield of 76%.

(5) The Preparation of 1-ethyl-5-methyl-3-pyrazolecarboxylic Acid

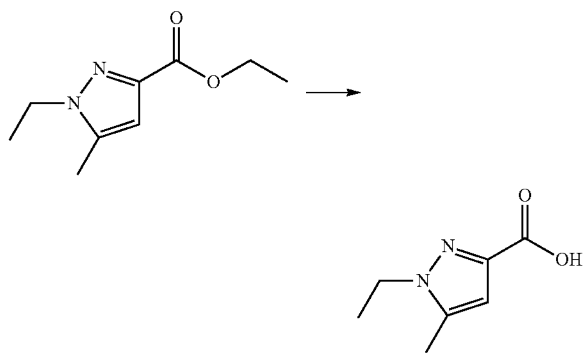

1-ethyl-5-methyl-3-pyrazole ethyl formate (1 g, 5.5 mmol) and ethanol (10 mL) were added to the reaction flask. 10% aqueous sodium hydroxide (2.5 mL) was slowly added to react at room temperature for 4 hours. The solvent was evaporated under reduced pressure. Water (10 mL) was added. Concentrated hydrochloric acid was used to adjust pH to 2-3, and the product was filtered and dried to obtain 0.7 g of yellow solid with a yield of 83%.

(6) The Preparation of 1-ethyl-5-methyl-3-pyrazole Formyl Chloride

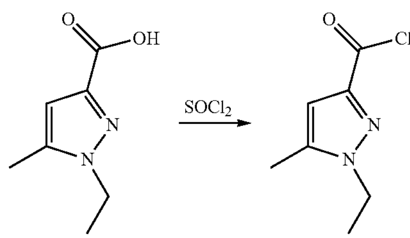

1-ethyl-5-methyl-3-pyrazolecarboxylic acid (0.5 g, 3.2 mmol) and toluene (20 mL) were added to the reaction flask, and thionyl chloride (1.9 g, 16 mmol) was slowly added. The mixture was refluxed for 4 hours, and the solvent was evaporated under reduced pressure to obtain 0.56 g of yellow oil, which was directly used in the next step.

(7) The Preparation of Compound 1-32

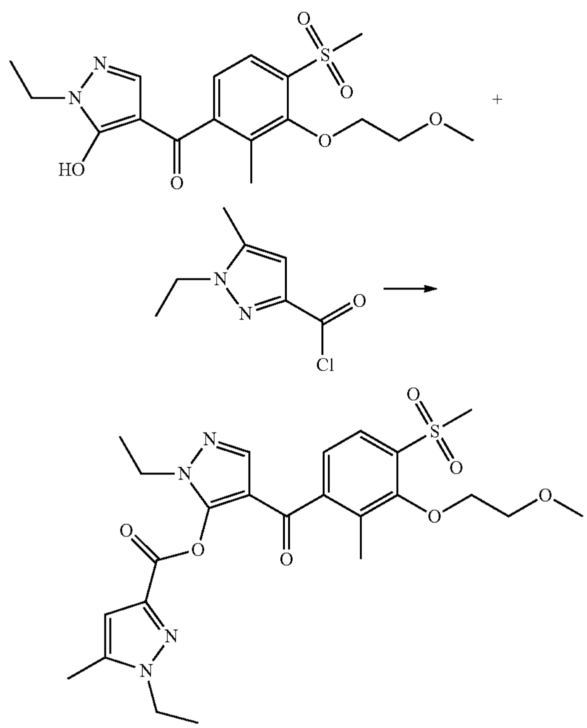

4-(2-methyl-3-methoxyethoxy-4-methylsulfuryl benzoyl)-1-ethyl-5-hydroxypyrazole (1.1 g, 2.9 mmol, in step 3 of example 1), dichloromethane (20 mL) and triethylamine (0.44 g, 4.4 mmol) were added to the reaction flask, and the dichloromethane solution (10 mL) of 1-ethyl-5-methyl-3-pyrazole formyl chloride in the above step was added dropwise. The mixture was stirred at room temperature for 1 hour. The solvent was evaporated under reduced pressure. Ethyl acetate (100 mL) and water (50 mL) was used for extraction. The organic phase was sequentially washed with saturated salt water (50 mL) and dried with anhydrous magnesium sulfate. The solvent was evaporated under reduced pressure, and the residue was separated by column chromatography to obtain 0.28 g of yellow oil, with a purity of 90% and a yield of 19%.

Example 2 the Preparation of Compound 1-139

(1) The Preparation of Compound 1-139

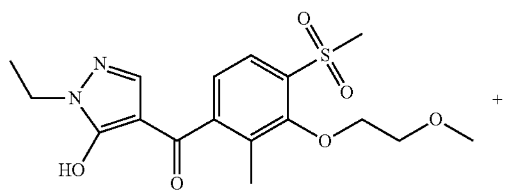

-continued

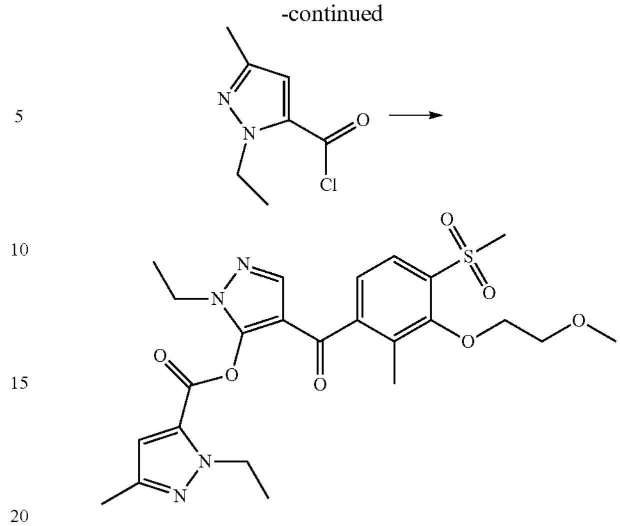

4-(2-methyl-3-methoxyethoxy-4-methylsulfuryl benzoyl)-1-ethyl-5-hydroxypyrazole (0.5 g, 1.3 mmol, in step 3 of example 1), dichloromethane (20 mL) and triethylamine (0.4 g, 3.9 mmol) were added to the reaction flask, and the dichloromethane solution (10 mL) of 1-ethyl-3-methyl-3-pyrazole formyl chloride (0.25 g, 1.44 mmol, prepared according to step 6 of example 1) was added dropwise. The mixture was stirred at room temperature for 1 hour. The solvent was evaporated under reduced pressure. Ethyl acetate (100 mL) and water (50 mL) was used for extraction. The organic phase was sequentially washed with saturated salt water (50 mL) and dried with anhydrous magnesium sulfate. The solvent was evaporated under reduced pressure, and the residue was separated by column chromatography to obtain 0.1 g of yellow oil, with a purity of 97% and a yield of 15%.

Example 3 the Preparation of Compound 1-95

(1) The Preparation of 2-chlorine-3-methoxypropoxy-4-methylsulfuryl Benzoyl Chloride

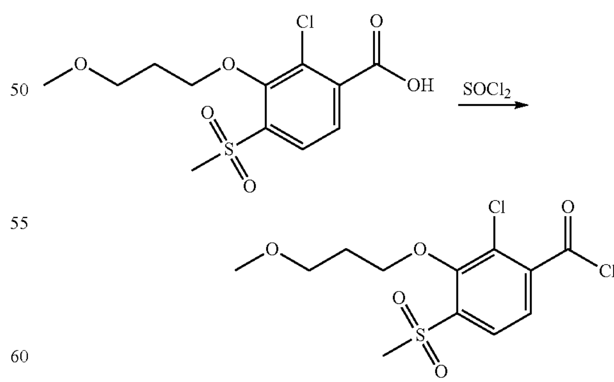

2-chlorine-3-methoxypropoxy-4-methylsulfuryl benzoic acid (1 g, 3.1 mmol, prepared according to CN86101277A) and toluene (20 mL) were added to a reaction flask, thionyl chloride (1.8 g, 15.5 mmol) was slowly added. The mixture was refluxed for 4 hours, and the solvent was evaporated under reduced pressure to obtain 1.1 g of yellow oil, which was directly used in the next step.

(2) The Preparation of 4-(2-chlorine-3-methoxypropoxy-4-methylsulfuryl benzoyl)-)-1,3-dimethyl-5-hydroxypyrazole

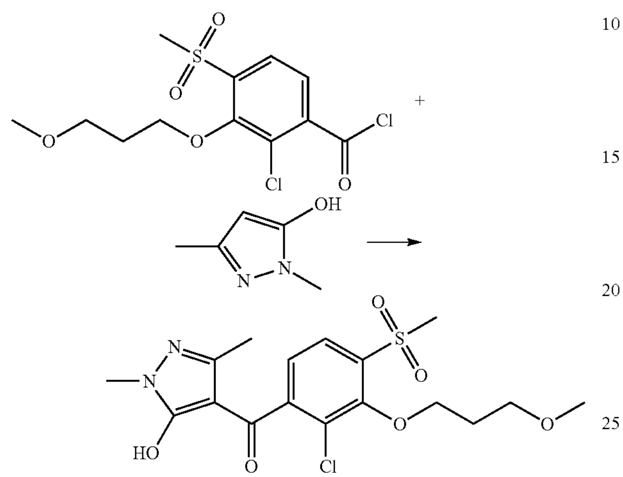

1,3-dimethyl-5-hydroxypyrazole (0.35 g, 3.1 mmol), dichloroethane (20 mL) and triethylamine (0.47 g, 4.6 mmol) were added to the reaction flask, and the dichloroethane solution (10 mL) of 2-chlorine-3-methoxypropoxy-4-methylsulfuryl benzoyl chloride in the above step was added dropwise. The mixture was stirred at room temperature for 2 hours. Triethylamine (0.47 g, 4.6 mmol) and 2 drops of acetone cyanohydrin were added. The mixture was stirred overnight at room temperature. Water (50 ml) was added to stir for half an hour. The aqueous phase was adjusted with 10% dilute hydrochloric acid to pH=2-3, and extracted with ethyl acetate (50 mL*2) twice. The combined organic phase was washed with saturated salt water (50 mL) and dried with anhydrous magnesium sulfate. The solvent was evaporated under reduced pressure, and the residue was separated by column chromatography to obtain 0.48 g of red oil with a purity of 90% and a yield of 39%.

$^1$H NMR (600 MHz, $CDCl_3$): 7.99 (d, 1H), 7.22 (d, 1H), 4.35 (t, 2H), 3.64 (s, 3H), 3.61 (t, 2H), 3.36 (s, 3H), 3.28 (s, 3H), 2.15-2.21 (m, 2H), 1.74 (s, 3H).

(3) The Preparation of 1-ethyl-5-methyl-3-pyrazole Formyl Chloride

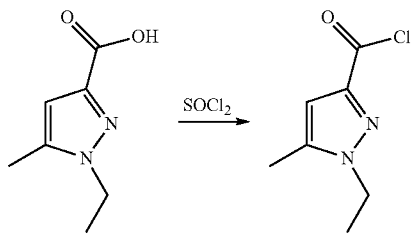

1-ethyl-5-methyl-3-pyrazolecarboxylic acid (0.22 g, 1.4 mmol, in step 5 of example 1) and toluene (20 mL) were added to the reaction flask, thionyl chloride (0.83 g, 7 mmol) was slowly added. The mixture was refluxed for 4 hours, and the solvent was evaporated under reduced pressure to obtain 0.23 g of yellow oil, which was directly used in the next step.

(4) The Preparation of Compound 1-95

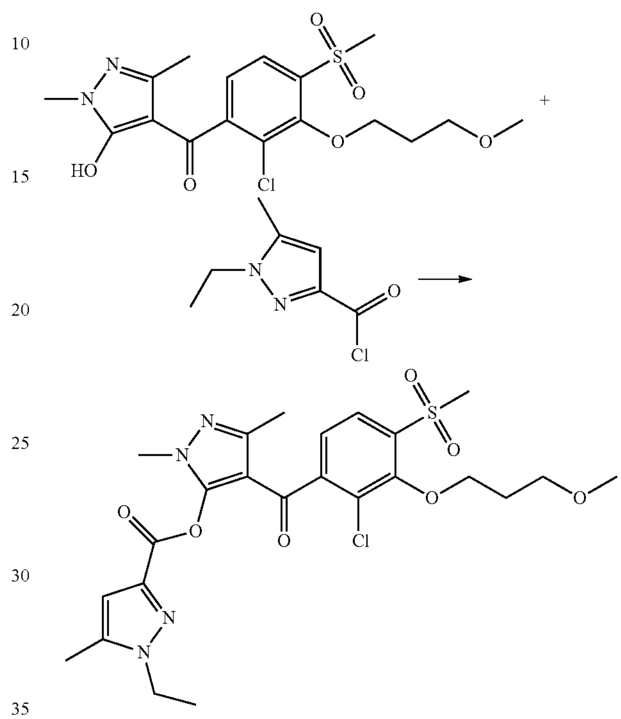

4-(2-chlorine-3-methoxypropoxy-4-methylsulfuryl benzoyl)-)-1, 3-dimethyl-5-hydroxypyrazole (0.48 g, 1.2 mmol), dichloromethane (20 ml) and triethylamine (0.2 g, 2 mmol) were added to the reaction flask, and the dichloromethane solution (10 mL) of 1-ethyl-5-methyl-3-pyrazole formyl chloride in the above step was added dropwise. The mixture was stirred at room temperature for 1 hour. The solvent was evaporated under reduced pressure. Ethyl acetate (100 mL) and water (50 mL) was used for extraction. The organic phase was sequentially washed with saturated salt water (50 mL) and dried with anhydrous magnesium sulfate. The solvent was evaporated under reduced pressure, and the residue was separated by column chromatography to obtain 0.46 g of white solid, with a purity of 96% and a yield of 69%.

Example 4 the Preparation of Compound 1-200

(1) The Preparation of Compound 1-200

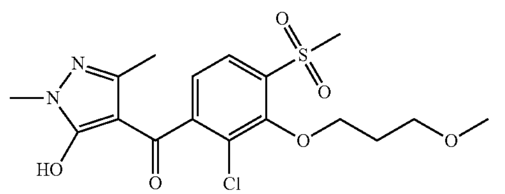

-continued

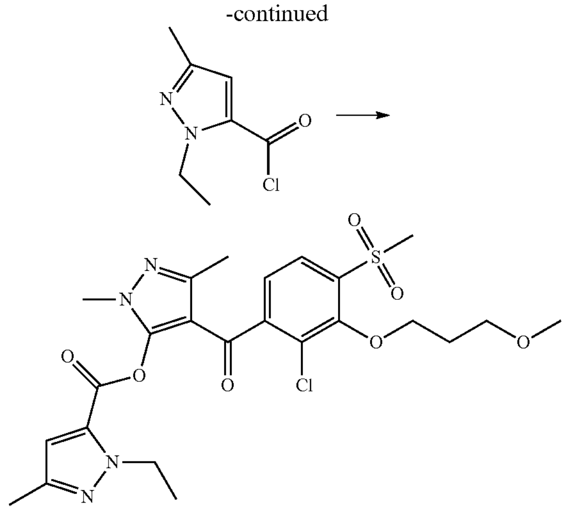

4-(2-chlorine-3-methoxypropoxy-4-methylsulfuryl benzoyl)-)-1,3-dimethyl-5-hydroxypyrazole (1 g, 2.4 mmol, in step 2 of example 3), dichloromethane (20 mL) and triethylamine (0.3 g, 3 mmol) were added to the reaction flask, and the dichloromethane solution (10 mL) of 1-ethyl-3-methyl-3-pyrazole formyl chloride (0.5 g, 2.9 mmol, prepared according to step 6 of example 1) was added dropwise. The mixture was stirred at room temperature for 1 hour. The solvent was evaporated under reduced pressure. Ethyl acetate (100 mL) and water (50 mL) was used for extraction. The organic phase was sequentially washed with saturated salt water (50 mL) and dried with anhydrous magnesium sulfate. The solvent was evaporated under reduced pressure. and the residue was separated by column chromatography to obtain 0.24 g of yellow oil, with a purity of 94% and a yield of 18%.

The initial substances are replaced according to the above recorded method to obtain other compounds shown by the formula I. Part of the compounds of the formula I can be found in Table 1.

The compounds of the general formula I, W is $CX_2$, $X_2$ is $Y_1$ oxy, $X_3$ is methylsulfonyl, $R_4$ is ethyl and Q is selected from $Q_1$ or $Q_3$.

I

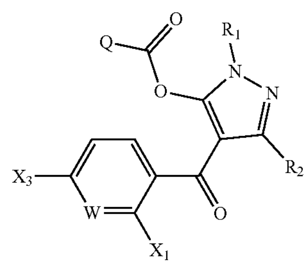

$Q_1$

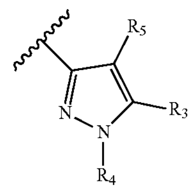

$Q_3$

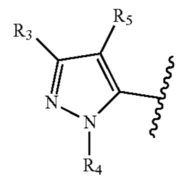

TABLE 1

Structures and Physical Properties of Part of Compounds of Formula I

| Compound | $X_1$ | $Y_1$ | Q | $R_1$ | $R_2$ | $R_3$ | $R_5$ | Appearance (Melting Point ° C.) |
|---|---|---|---|---|---|---|---|---|
| 1-1 | $CH_3$ | $CH_3$ | $Q_1$ | $CH_3$ | $CH_3$ | $CH_3$ | H | white solid (176-178) |
| 1-2 | $CH_3$ | $CH_3$ | $Q_1$ | $CH_3$ | H | $CH_3$ | H | yellow oil |
| 1-3 | $CH_3$ | $CH_3$ | $Q_1$ | $CH_2CH_3$ | H | $CH_3$ | H | yellow solid (117-119) |
| 1-4 | $CH_3$ | $CH_3$ | $Q_1$ | $CH_2CH_3$ | $CH_3$ | $CH_3$ | H | |
| 1-5 | $CH_3$ | $CH_3$ | $Q_1$ | $CH_3$ | 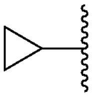 | $CH_3$ | H | |
| 1-6 | $CH_3$ | $CH_3$ | $Q_1$ | $CH_3$ | 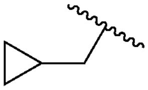 | $CH_3$ | H | |
| 1-7 | $CH_3$ | $CH_3$ | $Q_1$ | $CH_3$ | $CH_3$ | 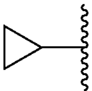 | H | |
| 1-8 | $CH_3$ | $CH_3$ | $Q_1$ | $CH_3$ | $CH_3$ | $CH_3$ | Cl | |
| 1-9 | $CH_3$ | $CH_2CH_3$ | $Q_1$ | $CH_3$ | H | $CH_3$ | H | pale yellow solid (164-166) |
| 1-10 | $CH_3$ | $CH_2CH_3$ | $Q_1$ | $CH_3$ | $CH_3$ | $CH_3$ | H | white solid (156-157) |

TABLE 1-continued

Structures and Physical Properties of Part of Compounds of Formula I

| Compound | $X_1$ | $Y_1$ | Q | $R_1$ | $R_2$ | $R_3$ | $R_5$ | Appearance (Melting Point ° C.) |
|---|---|---|---|---|---|---|---|---|
| 1-11 | $CH_3$ | $CH_2CH_3$ | $Q_1$ | $CH_2CH_3$ | H | $CH_3$ | H | orange yellow solid (177-179) |
| 1-12 | $CH_3$ | $CH_2CH_3$ | $Q_1$ | $CH_2CH_3$ | $CH_3$ | $CH_3$ | H | white solid (174-176) |
| 1-13 | $CH_3$ | $CH_2CH_3$ | $Q_1$ | $CH_3$ | 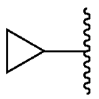 [SMILES: *C1CC1] | $CH_3$ | H | |
| 1-14 | $CH_3$ | $CH_2CH_3$ | $Q_1$ | $CH_3$ | 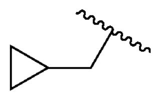 | $CH_3$ | H | |
| 1-15 | $CH_3$ | $CH_2CH_3$ | $Q_1$ | $CH_3$ | $CH_3$ | 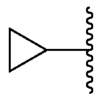 [SMILES: *C1CC1] | H | |
| 1-16 | $CH_3$ | $CH_2CH_3$ | $Q_1$ | $CH_3$ | $CH_3$ | $CH_3$ | $CH_3$ | |
| 1-17 | $CH_3$ | 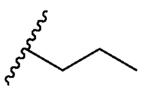 [SMILES: *CCC] | $Q_1$ | $CH_3$ | $CH_3$ | $CH_3$ | H | colorless oil |
| 1-18 | $CH_3$ | 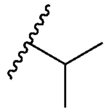 [SMILES: *C(C)C] | $Q_1$ | $CH_3$ | $CH_3$ | $CH_3$ | H | pale yellow solid (132-134) |
| 1-19 | $CH_3$ | 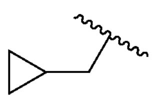 [SMILES: *CC1CC1] | $Q_1$ | $CH_3$ | H | $CH_3$ | H | pale yellow solid (160-162) |
| 1-20 | $CH_3$ | 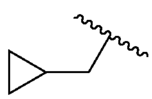 [SMILES: *CC1CC1] | $Q_1$ | $CH_3$ | $CH_3$ | $CH_3$ | H | colorless oil |
| 1-21 | $CH_3$ | 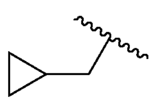 [SMILES: *CC1CC1] | $Q_1$ | $CH_2CH_3$ | H | $CH_3$ | H | |
| 1-22 | $CH_3$ | 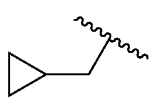 [SMILES: *CC1CC1] | $Q_1$ | $CH_2CH_3$ | $CH_3$ | $CH_3$ | H | |
| 1-23 | $CH_3$ | 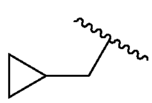 [SMILES: *CC1CC1] | $Q_1$ | $CH_3$ | 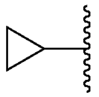 [SMILES: *C1CC1] | $CH_3$ | H | |
| 1-24 | $CH_3$ | 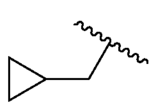 [SMILES: *CC1CC1] | $Q_1$ | $CH_3$ | 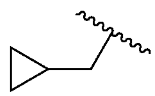 [SMILES: *CC1CC1] | $CH_3$ | H | |
| 1-25 | $CH_3$ | 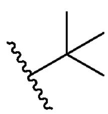 [SMILES: *C(C)(C)C] | $Q_1$ | $CH_3$ | $CH_3$ | $CH_3$ | H | |

TABLE 1-continued

| Compound | $X_1$ | $Y_1$ | Q | $R_1$ | $R_2$ | $R_3$ | $R_5$ | Appearance (Melting Point ° C.) |
|---|---|---|---|---|---|---|---|---|
| Structures and Physical Properties of Part of Compounds of Formula I | | | | | | | | |
| 1-26 | $CH_3$ | 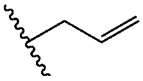 [SMILES: *CC=C] | $Q_1$ | $CH_3$ | $CH_3$ | $CH_3$ | H | white solid (165-167) |
| 1-27 | $CH_3$ | 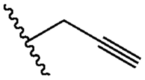 [SMILES: *CC#C] | $Q_1$ | $CH_3$ | $CH_3$ | $CH_3$ | H | white solid (176-178) |
| 1-28 | $CH_3$ | 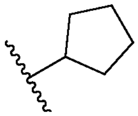 [SMILES: *C1CCCC1] | $Q_1$ | $CH_3$ | $CH_3$ | $CH_3$ | H | |
| 1-29 | $CH_3$ | 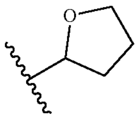 [SMILES: *C1CCCO1] | $Q_1$ | $CH_3$ | $CH_3$ | $CH_3$ | H | |
| 1-30 | $CH_3$ | 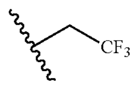 [SMILES: *CC(F)(F)F] | $Q_1$ | $CH_3$ | $CH_3$ | $CH_3$ | H | white solid (153-154) |
| 1-31 | $CH_3$ | 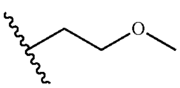 [SMILES: *CCOC] | $Q_1$ | $CH_3$ | H | $CH_3$ | H | colorless oil |
| 1-32 | $CH_3$ | 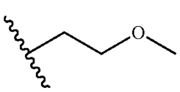 [SMILES: *CCOC] | $Q_1$ | $CH_2CH_3$ | H | $CH_3$ | H | yellow oil |
| 1-33 | $CH_3$ | 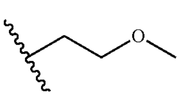 [SMILES: *CCOC] | $Q_1$ | $CH_3$ | $CH_3$ | $CH_3$ | H | yellow oil |
| 1-34 | $CH_3$ | 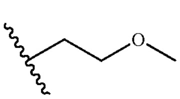 [SMILES: *CCOC] | $Q_1$ | 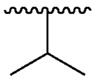 | $CH_3$ | $CH_3$ | H | yellow solid (157-159) |
| 1-35 | $CH_3$ | 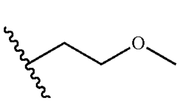 [SMILES: *CCOC] | $Q_1$ | $CH_3$ | $CHF_2$ | $CH_3$ | H | yellow solid (198-200) |
| 1-36 | $CH_3$ | 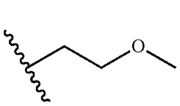 [SMILES: *CCOC] | $Q_1$ | $CH_3$ | $CH_2CH_3$ | $CH_3$ | H | yellow solid (133-134) |
| 1-37 | $CH_3$ | 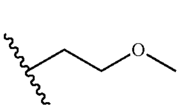 [SMILES: *CCOC] | $Q_1$ | $CH_2CH_3$ | $CH_3$ | $CH_3$ | H | yellow solid (147-149) |
| 1-38 | $CH_3$ | 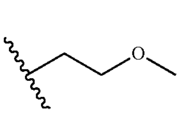 [SMILES: *CCOC] | $Q_1$ | $CH_3$ | 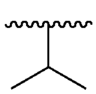 | $CH_3$ | H | white solid (141-142) |
| 1-39 | $CH_3$ | 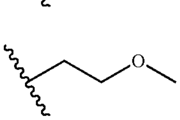 | $Q_1$ | $CH_3$ | 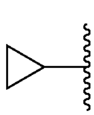 | $CH_3$ | H | yellow solid (116-117) |

TABLE 1-continued

| Structures and Physical Properties of Part of Compounds of Formula I | | | | | | | | |
|---|---|---|---|---|---|---|---|---|
| Compound | $X_1$ | $Y_1$ | Q | $R_1$ | $R_2$ | $R_3$ | $R_5$ | Appearance (Melting Point ° C.) |
| 1-40 | $CH_3$ | 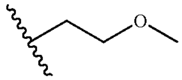 [SMILES: *CCOC] | $Q_1$ | $CH_2CH_3$ | 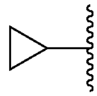 [SMILES: *C1CC1] | $CH_3$ | H | |
| 1-41 | $CH_3$ | 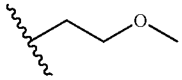 [SMILES: *CCOC] | $Q_1$ | $CH_3$ | 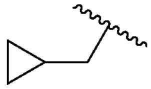 [SMILES: *CC1CC1] | $CH_3$ | H | pale yellow solid (105-107) |
| 1-42 | $CH_3$ | 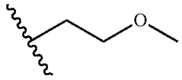 [SMILES: *CCOC] | $Q_1$ | $CH_3$ | $CH_3$ | 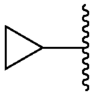 [SMILES: *C1CC1] | H | |
| 1-43 | $CH_3$ | 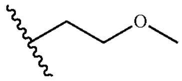 [SMILES: *CCOC] | $Q_1$ | $CH_3$ | $CH_3$ | $CH_3$ | Cl | |
| 1-44 | $CH_3$ | 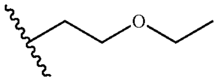 [SMILES: *CCOCC] | $Q_1$ | $CH_3$ | $CH_3$ | $CH_3$ | H | colorless oil |
| 1-45 | $CH_3$ | 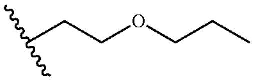 [SMILES: *CCOCCC] | $Q_1$ | $CH_3$ | $CH_3$ | $CH_3$ | H | |
| 1-46 | CH3 | 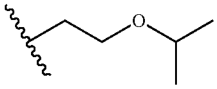 [SMILES: *CCOC(C)C] | $Q_1$ | $CH_3$ | $CH_3$ | $CH_3$ | H | |
| 1-47 | $CH_3$ | 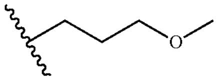 [SMILES: *CCCOC] | $Q_1$ | $CH_3$ | H | $CH_3$ | H | |
| 1-48 | $CH_3$ | 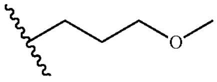 [SMILES: *CCCOC] | $Q_1$ | $CH_3$ | $CH_3$ | $CH_3$ | H | colorless oil |
| 1-49 | $CH_3$ | 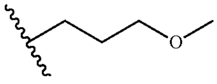 [SMILES: *CCCOC] | $Q_1$ | $CH_2CH_3$ | H | $CH_3$ | H | |
| 1-50 | $CH_3$ | 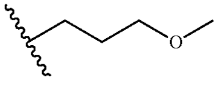 [SMILES: *CCCOC] | $Q_1$ | $CH_2CH_3$ | $CH_3$ | $CH_3$ | H | |
| 1-51 | $CH_3$ | 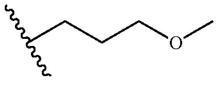 [SMILES: *CCCOC] | $Q_1$ | $CH_3$ | 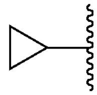 [SMILES: *C1CC1] | $CH_3$ | H | |
| 1-52 | $CH_3$ | 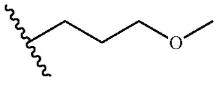 [SMILES: *CCCOC] | $Q_1$ | $CH_3$ | 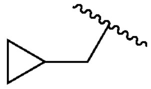 [SMILES: *CC1CC1] | $CH_3$ | H | |
| 1-53 | $CH_3$ | 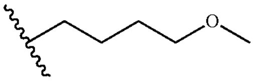 [SMILES: *CCCCOC] | $Q_1$ | $CH_3$ | $CH_3$ | $CH_3$ | H | white solid (152-154) |

TABLE 1-continued

| Structures and Physical Properties of Part of Compounds of Formula I | | | | | | | | |
|---|---|---|---|---|---|---|---|---|
| Compound | $X_1$ | $Y_1$ | Q | $R_1$ | $R_2$ | $R_3$ | $R_5$ | Appearance (Melting Point ° C.) |
| 1-54 | $CH_3$ | 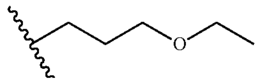 [SMILES: *CCCOCC] | $Q_1$ | $CH_3$ | $CH_3$ | $CH_3$ | H | |
| 1-55 | $CH_3$ | 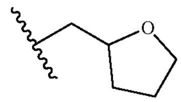 [SMILES: *CC1CCCO1] | $Q_1$ | $CH_3$ | $CH_3$ | $CH_3$ | H | white solid (147-149) |
| 1-56 | $CH_3$ | 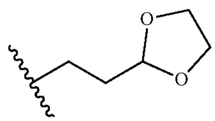 [SMILES: *CCC1OCCO1] | $Q_1$ | $CH_3$ | $CH_3$ | $CH_3$ | H | |
| 1-57 | $CH_3$ | 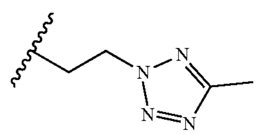 [SMILES: *CCn1nnc(C)n1] | $Q_1$ | $CH_3$ | $CH_3$ | $CH_3$ | H | |
| 1-58 | $CH_3$ | 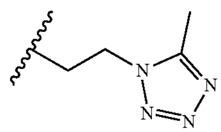 [SMILES: *CCn1nnnc1C] | $Q_1$ | $CH_3$ | 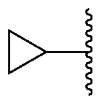 [SMILES: *C1CC1] | $CH_3$ | H | |
| 1-59 | Cl | $CH_3$ | $Q_1$ | $CH_3$ | H | $CH_3$ | H | |
| 1-60 | Cl | $CH_3$ | $Q_1$ | $CH_3$ | $CH_3$ | $CH_3$ | H | colorless oil |
| 1-61 | Cl | $CH_3$ | $Q_1$ | $CH_2CH_3$ | H | $CH_3$ | H | |
| 1-62 | Cl | $CH_3$ | $Q_1$ | $CH_2CH_3$ | $CH_3$ | $CH_3$ | H | |
| 1-63 | Cl | $CH_3$ | $Q_1$ | $CH_3$ | 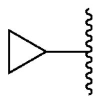 [SMILES: *C1CC1] | $CH_3$ | H | |
| 1-64 | Cl | $CH_3$ | $Q_1$ | $CH_3$ | 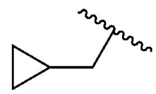 [SMILES: *CC1CC1] | $CH_3$ | H | |
| 1-65 | Cl | $CH_2CH_3$ | $Q_1$ | $CH_3$ | H | $CH_3$ | H | colorless oil |
| 1-66 | Cl | $CH_2CH_3$ | $Q_1$ | $CH_3$ | $CH_3$ | $CH_3$ | H | colorless oil |
| 1-67 | Cl | $CH_2CH_3$ | $Q_1$ | $CH_2CH_3$ | H | $CH_3$ | H | brown oil |
| 1-68 | Cl | $CH_2CH_3$ | $Q_1$ | $CH_2CH_3$ | $CH_3$ | $CH_3$ | H | white solid (156-158) |
| 1-69 | Cl | $CH_2CH_3$ | $Q_1$ | $CH_3$ | 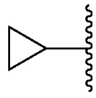 [SMILES: *C1CC1] | $CH_3$ | H | |
| 1-70 | Cl | $CH_2CH_3$ | $Q_1$ | $CH_3$ | 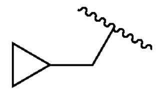 [SMILES: *CC1CC1] | $CH_3$ | H | |
| 1-71 | Cl | $CH_2CH_3$ | $Q_1$ | $CH_3$ | $CH_3$ | 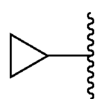 [SMILES: *C1CC1] | H | |
| 1-72 | Cl | $CH_2CH_3$ | $Q_1$ | $CH_3$ | $CH_3$ | $CH_3$ | Cl | |
| 1-73 | Cl | 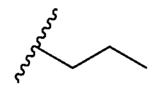 [SMILES: *CCC] | $Q_1$ | $CH_3$ | $CH_3$ | $CH_3$ | H | colorless oil |

TABLE 1-continued

| Structures and Physical Properties of Part of Compounds of Formula I | | | | | | | | |
|---|---|---|---|---|---|---|---|---|
| Compound | $X_1$ | $Y_1$ | Q | $R_1$ | $R_2$ | $R_3$ | $R_5$ | Appearance (Melting Point ° C.) |
| 1-74 | Cl | 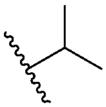 [SMILES: *C(C)C] | $Q_1$ | $CH_3$ | $CH_3$ | $CH_3$ | H | yellow oil |
| 1-75 | Cl | 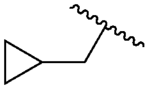 [SMILES: *CC1CC1] | $Q_1$ | $CH_3$ | H | $CH_3$ | H | |
| 1-76 | Cl | 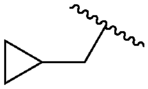 [SMILES: *CC1CC1] | $Q_1$ | $CH_3$ | $CH_3$ | $CH_3$ | H | yellow oil |
| 1-77 | Cl | 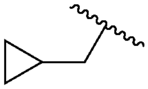 [SMILES: *CC1CC1] | $Q_1$ | $CH_2CH_3$ | H | $CH_3$ | H | |
| 1-78 | Cl | 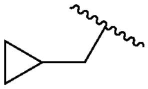 [SMILES: *CC1CC1] | $Q_1$ | $CH_2CH_3$ | $CH_3$ | $CH_3$ | H | |
| 1-79 | Cl | 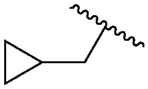 [SMILES: *CC1CC1] | $Q_1$ | $CH_3$ | 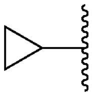 [SMILES: *C1CC1] | $CH_3$ | H | |
| 1-80 | Cl | 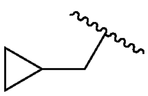 [SMILES: *CC1CC1] | $Q_1$ | $CH_3$ | 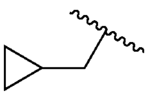 [SMILES: *CC1CC1] | $CH_3$ | H | |
| 1-81 | Cl | 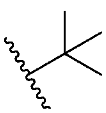 [SMILES: *C(C)(C)C] | $Q_1$ | $CH_3$ | $CH_3$ | $CH_3$ | H | |
| 1-82 | Cl | 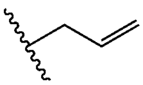 [SMILES: *CC=C] | $Q_1$ | $CH_3$ | $CH_3$ | $CH_3$ | H | colorless oil |
| 1-83 | Cl | 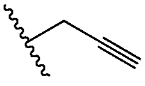 [SMILES: *CC#C] | $Q_1$ | $CH_3$ | $CH_3$ | $CH_3$ | H | colorless oil |
| 1-84 | Cl | 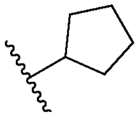 [SMILES: *C1CCCC1] | $Q_1$ | $CH_3$ | $CH_3$ | $CH_3$ | H | |
| 1-85 | Cl | 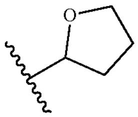 [SMILES: *C1CCCO1] | $Q_1$ | $CH_3$ | $CH_3$ | $CH_3$ | H | |
| 1-86 | Cl | 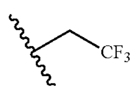 [SMILES: *CC(F)(F)F] | $Q_1$ | $CH_3$ | $CH_3$ | $CH_3$ | H | |

TABLE 1-continued

Structures and Physical Properties of Part of Compounds of Formula I

| Compound | $X_1$ | $Y_1$ | Q | $R_1$ | $R_2$ | $R_3$ | $R_5$ | Appearance (Melting Point ° C.) |
|---|---|---|---|---|---|---|---|---|
| 1-87 | Cl | 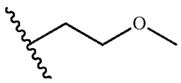 [SMILES: *CCOC] | $Q_1$ | $CH_3$ | H | $CH_3$ | H | yellow oil |
| 1-88 | Cl | 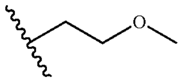 [SMILES: *CCOC] | $Q_1$ | $CH_3$ | $CH_3$ | $CH_3$ | H | colorless oil |
| 1-89 | Cl | 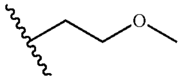 [SMILES: *CCOC] | $Q_1$ | $CH_2CH_3$ | H | $CH_3$ | H | yellow oil |
| 1-90 | Cl | 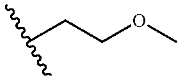 [SMILES: *CCOC] | $Q_1$ | $CH_2CH_3$ | $CH_3$ | $CH_3$ | H | white solid (166-168) |
| 1-91 | Cl | 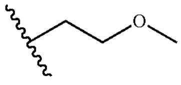 [SMILES: *CCOC] | $Q_1$ | $CH_3$ | 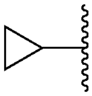 [SMILES: *C1CC1] | $CH_3$ | H | |
| 1-92 | Cl | 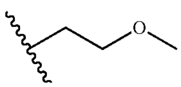 [SMILES: *CCOC] | $Q_1$ | $CH_3$ | 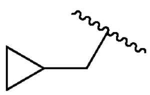 [SMILES: *CC1CC1] | $CH_3$ | H | |
| 1-93 | Cl | 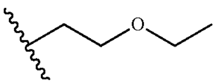 [SMILES: *CCOCC] | $Q_1$ | $CH_3$ | $CH_3$ | $CH_3$ | H | white solid (131-133) |
| 1-94 | Cl | 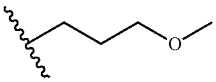 [SMILES: *CCCOC] | $Q_1$ | $CH_3$ | H | $CH_3$ | H | yellow oil |
| 1-95 | Cl | 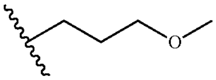 [SMILES: *CCCOC] | $Q_1$ | $CH_3$ | $CH_3$ | $CH_3$ | H | white solid (123-125) |
| 1-96 | Cl | 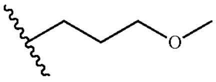 [SMILES: *CCCOC] | $Q_1$ | $CH_2CH_3$ | H | $CH_3$ | H | yellow oil |
| 1-97 | Cl | 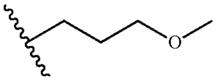 [SMILES: *CCCOC] | $Q_1$ | $CH_2CH_3$ | $CH_3$ | $CH_3$ | H | |
| 1-98 | Cl | 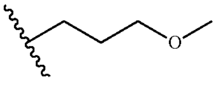 [SMILES: *CCCOC] | $Q_1$ | $CH_3$ | 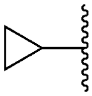 [SMILES: *C1CC1] | $CH_3$ | H | |
| 1-99 | Cl | 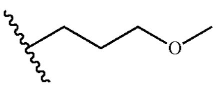 [SMILES: *CCCOC] | $Q_1$ | $CH_3$ | 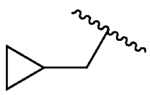 | $CH_3$ | H | |
| 1-100 | Cl | 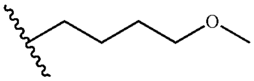 [SMILES: *CCCCOC] | $Q_1$ | $CH_3$ | $CH_3$ | $CH_3$ | H | white solid (119-121) |
| 1-101 | Cl | 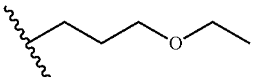 [SMILES: *CCCOCC] | $Q_1$ | $CH_3$ | $CH_3$ | $CH_3$ | H | |

TABLE 1-continued

| Structures and Physical Properties of Part of Compounds of Formula I | | | | | | | | |
|---|---|---|---|---|---|---|---|---|
| Compound | $X_1$ | $Y_1$ | Q | $R_1$ | $R_2$ | $R_3$ | $R_5$ | Appearance (Melting Point ° C.) |
| 1-102 | Cl | 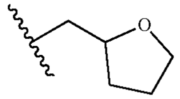 [SMILES: *CC1CCCO1] | $Q_1$ | $CH_3$ | $CH_3$ | $CH_3$ | H | white solid (119-121) |
| 1-103 | Cl | 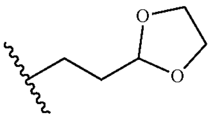 [SMILES: *CCC1OCCO1] | $Q_1$ | $CH_3$ | H | $CH_3$ | H | |
| 1-104 | Cl | 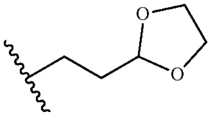 [SMILES: *CCC1OCCO1] | $Q_1$ | $CH_2CH_3$ | H | $CH_3$ | H | |
| 1-105 | Cl | 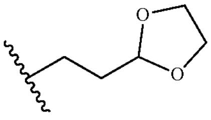 [SMILES: *CCC1OCCO1] | $Q_1$ | $CH_3$ | $CH_3$ | $CH_3$ | H | |
| 1-106 | Cl | 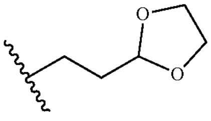 [SMILES: *CCC1OCCO1] | $Q_1$ | $CH_2CH_3$ | $CH_3$ | $CH_3$ | H | |
| 1-107 | Cl | 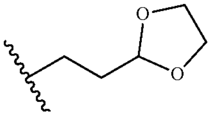 [SMILES: *CCC1OCCO1] | $Q_1$ | $CH_3$ | 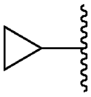 [SMILES: *C1CC1] | $CH_3$ | H | |
| 1-108 | Cl | 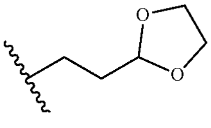 [SMILES: *CCC1OCCO1] | $Q_1$ | $CH_2CH_3$ | 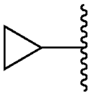 [SMILES: *C1CC1] | $CH_3$ | H | |
| 1-109 | Cl | 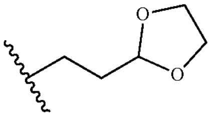 [SMILES: *CCC1OCCO1] | $Q_1$ | $CH_3$ | 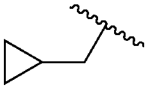 [SMILES: *CC1CC1] | $CH_3$ | H | |
| 1-110 | Cl | 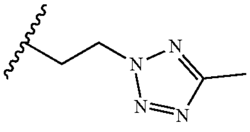 [SMILES: *CCn1nnc(C)n1] | $Q_1$ | $CH_3$ | $CH_3$ | $CH_3$ | H | |
| 1-111 | Cl | 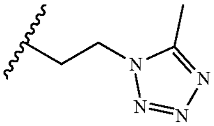 [SMILES: *CCn1nnnc1C] | $Q_1$ | $CH_3$ | 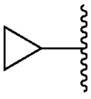 [SMILES: *C1CC1] | $CH_3$ | H | |
| 1-112 | $CH_3$ | $CH_3$ | $Q_3$ | $CH_3$ | $CH_3$ | $CH_3$ | H | white solid (158-161) |
| 1-113 | $CH_3$ | $CH_3$ | $Q_3$ | $CH_3$ | H | $CH_3$ | H | pale yellow solid (89-91) |
| 1-114 | $CH_3$ | $CH_3$ | $Q_3$ | $CH_2CH_3$ | H | $CH_3$ | H | pale yellow solid (165-167) |
| 1-115 | $CH_3$ | $CH_3$ | $Q_3$ | $CH_2CH_3$ | $CH_3$ | $CH_3$ | H | |

TABLE 1-continued

| Structures and Physical Properties of Part of Compounds of Formula I | | | | | | | | |
|---|---|---|---|---|---|---|---|---|
| Compound | $X_1$ | $Y_1$ | Q | $R_1$ | $R_2$ | $R_3$ | $R_5$ | Appearance (Melting Point ° C.) |
| 1-116 | $CH_3$ | $CH_3$ | $Q_3$ | $CH_3$ | 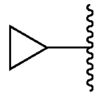 [SMILES: *C1CC1] | $CH_3$ | H | |
| 1-117 | $CH_3$ | $CH_3$ | $Q_3$ | $CH_3$ | 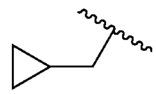 | $CH_3$ | H | |
| 1-118 | $CH_3$ | $CH_2CH_3$ | $Q_3$ | $CH_3$ | H | $CH_3$ | H | orange yellow solid (144-146) |
| 1-119 | $CH_3$ | $CH_2CH_3$ | $Q_3$ | $CH_3$ | $CH_3$ | $CH_3$ | H | yellow solid (143-145) |
| 1-120 | $CH_3$ | $CH_2CH_3$ | $Q_3$ | $CH_2CH_3$ | H | $CH_3$ | H | orange yellow solid (127-130) |
| 1-121 | $CH_3$ | $CH_2CH_3$ | $Q_3$ | $CH_2CH_3$ | $CH_3$ | $CH_3$ | H | white solid (154-156) |
| 1-122 | $CH_3$ | $CH_2CH_3$ | $Q_3$ | $CH_3$ | 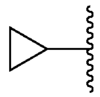 [SMILES: *C1CC1] | $CH_3$ | H | |
| 1-123 | $CH_3$ | $CH_2CH_3$ | $Q_3$ | $CH_3$ | 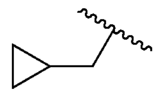 [SMILES: *CC1CC1] | $CH_3$ | H | |
| 1-124 | $CH_3$ | 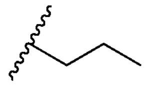 | $Q_3$ | $CH_3$ | $CH_3$ | $CH_3$ | H | |
| 1-125 | $CH_3$ | 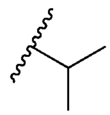 | $Q_3$ | $CH_3$ | $CH_3$ | $CH_3$ | H | |
| 1-126 | $CH_3$ | 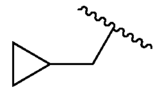 [SMILES: *CC1CC1] | $Q_3$ | $CH_3$ | H | $CH_3$ | H | pale yellow solid (126-128) |
| 1-127 | $CH_3$ | 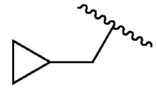 [SMILES: *CC1CC1] | $Q_3$ | $CH_3$ | $CH_3$ | $CH_3$ | H | yellow oil |
| 1-128 | $CH_3$ | 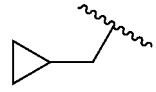 | $Q_3$ | $CH_2CH_3$ | H | $CH_3$ | H | yellow oil |
| 1-129 | $CH_3$ | 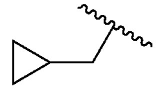 [SMILES: *CC1CC1] | $Q_3$ | $CH_2CH_3$ | $CH_3$ | $CH_3$ | H | |
| 1-130 | $CH_3$ | 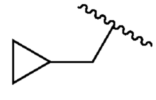 [SMILES: *CC1CC1] | $Q_3$ | $CH_3$ | 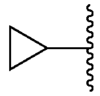 [SMILES: *C1CC1] | $CH_3$ | H | |
| 1-131 | $CH_3$ | 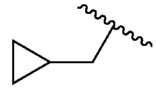 [SMILES: *CC1CC1] | $Q_3$ | $CH_3$ | 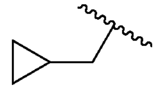 [SMILES: *CC1CC1] | $CH_3$ | H | |

TABLE 1-continued

| Structures and Physical Properties of Part of Compounds of Formula I | | | | | | | | |
|---|---|---|---|---|---|---|---|---|
| Compound | $X_1$ | $Y_1$ | Q | $R_1$ | $R_2$ | $R_3$ | $R_5$ | Appearance (Melting Point ° C.) |
| 1-132 | $CH_3$ | 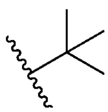 [SMILES: *C(C)(C)C] | $Q_3$ | $CH_3$ | $CH_3$ | $CH_3$ | H | |
| 1-133 | $CH_3$ | 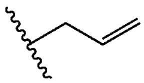 [SMILES: *CC=C] | $Q_3$ | $CH_3$ | $CH_3$ | $CH_3$ | H | |
| 1-134 | $CH_3$ | 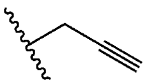 [SMILES: *CC#C] | $Q_3$ | $CH_3$ | $CH_3$ | $CH_3$ | H | |
| 1-135 | $CH_3$ | 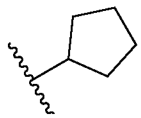 [SMILES: *C1CCCC1] | $Q_3$ | $CH_3$ | $CH_3$ | $CH_3$ | H | |
| 1-136 | $CH_3$ | 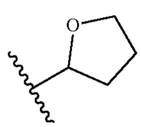 [SMILES: *C1CCCO1] | $Q_3$ | $CH_3$ | $CH_3$ | $CH_3$ | H | |
| 1-137 | $CH_3$ | 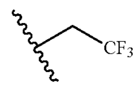 | $Q_3$ | $CH_3$ | $CH_3$ | $CH_3$ | H | |
| 1-138 | $CH_3$ | 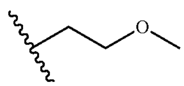 [SMILES: *CCOC] | $Q_3$ | $CH_3$ | H | $CH_3$ | H | white solid (158-160) |
| 1-139 | $CH_3$ | 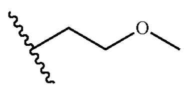 [SMILES: *CCOC] | $Q_3$ | $CH_2CH_3$ | H | $CH_3$ | H | yellow oil |
| 1-140 | $CH_3$ | 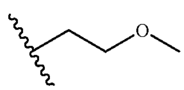 [SMILES: *CCOC] | $Q_3$ | $CH_3$ | $CH_3$ | $CH_3$ | H | yellow solid (120-121) |
| 1-141 | $CH_3$ | 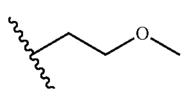 [SMILES: *CCOC] | $Q_3$ | 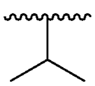 | $CH_3$ | $CH_3$ | H | |
| 1-142 | $CH_3$ | 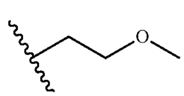 [SMILES: *CCOC] | $Q_3$ | $CH_3$ | $CHF_2$ | $CH_3$ | H | |
| 1-143 | $CH_3$ | 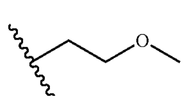 [SMILES: *CCOC] | $Q_3$ | $CH_3$ | $CH_2CH_3$ | $CH_3$ | H | |
| 1-144 | $CH_3$ | 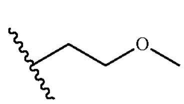 [SMILES: *CCOC] | $Q_3$ | $CH_2CH_3$ | $CH_3$ | $CH_3$ | H | white solid (127-129) |
| 1-145 | $CH_3$ | 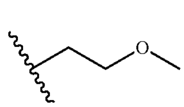 [SMILES: *CCOC] | $Q_3$ | $CH_3$ | 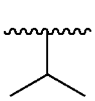 | $CH_3$ | H | |

TABLE 1-continued

Structures and Physical Properties of Part of Compounds of Formula I

| Compound | $X_1$ | $Y_1$ | Q | $R_1$ | $R_2$ | $R_3$ | $R_5$ | Appearance (Melting Point ° C.) |
|---|---|---|---|---|---|---|---|---|
| 1-146 | $CH_3$ | 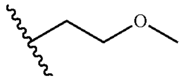 [SMILES: *CCOC] | $Q_3$ | $CH_3$ | 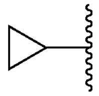 [SMILES: *C1CC1] | $CH_3$ | H | |
| 1-147 | $CH_3$ | 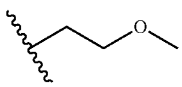 [SMILES: *CCOC] | $Q_3$ | $CH_2CH_3$ | 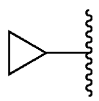 [SMILES: *C1CC1] | $CH_3$ | H | |
| 1-148 | $CH_3$ | 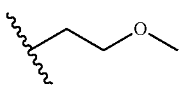 [SMILES: *CCOC] | $Q_3$ | $CH_3$ | 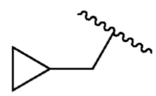 [SMILES: *CC1CC1] | $CH_3$ | H | yellow oil |
| 1-149 | $CH_3$ | 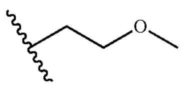 [SMILES: *CCOC] | $Q_3$ | $CH_3$ | $CH_3$ | 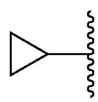 [SMILES: *C1CC1] | H | |
| 1-150 | $CH_3$ | 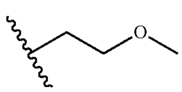 [SMILES: *CCOC] | $Q_3$ | $CH_3$ | $CH_3$ | $CH_3$ | Cl | |
| 1-151 | $CH_3$ | 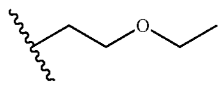 [SMILES: *CCOCC] | $Q_3$ | $CH_3$ | $CH_3$ | $CH_3$ | H | |
| 1-152 | $CH_3$ | 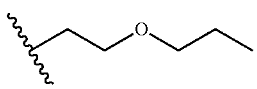 [SMILES: *CCOCCC] | $Q_3$ | $CH_3$ | $CH_3$ | $CH_3$ | H | |
| 1-153 | $CH_3$ | 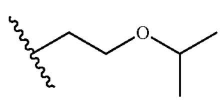 [SMILES: *CCOC(C)C] | $Q_3$ | $CH_3$ | $CH_3$ | $CH_3$ | H | |
| 1-154 | $CH_3$ | 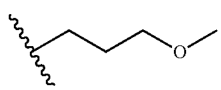 [SMILES: *CCCOC] | $Q_3$ | $CH_3$ | H | $CH_3$ | H | |
| 1-155 | $CH_3$ | 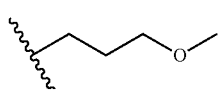 [SMILES: *CCCOC] | $Q_3$ | $CH_3$ | $CH_3$ | $CH_3$ | H | |
| 1-156 | $CH_3$ | 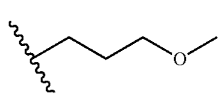 [SMILES: *CCCOC] | $Q_3$ | $CH_2CH_3$ | H | $CH_3$ | H | |
| 1-157 | $CH_3$ | 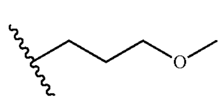 [SMILES: *CCCOC] | $Q_3$ | $CH_2CH_3$ | $CH_3$ | $CH_3$ | H | |
| 1-158 | $CH_3$ | 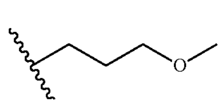 [SMILES: *CCCOC] | $Q_3$ | $CH_3$ | 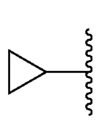 [SMILES: *C1CC1] | $CH_3$ | H | |
| 1-159 | $CH_3$ | 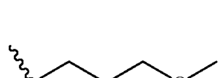 | $Q_3$ | $CH_3$ | 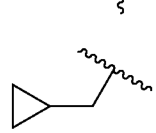 | $CH_3$ | H | |

TABLE 1-continued

Structures and Physical Properties of Part of Compounds of Formula I

| Compound | $X_1$ | $Y_1$ | Q | $R_1$ | $R_2$ | $R_3$ | $R_5$ | Appearance (Melting Point ° C.) |
|---|---|---|---|---|---|---|---|---|
| 1-160 | $CH_3$ | 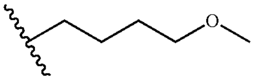 [SMILES: *CCCCOC] | $Q_3$ | $CH_3$ | $CH_3$ | $CH_3$ | H | |
| 1-161 | $CH_3$ | 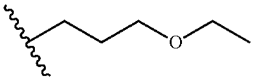 [SMILES: *CCCOCC] | $Q_3$ | $CH_3$ | $CH_3$ | $CH_3$ | H | |
| 1-162 | $CH_3$ | 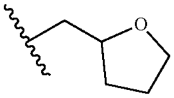 [SMILES: *CC1CCCO1] | $Q_3$ | $CH_3$ | $CH_3$ | $CH_3$ | H | |
| 1-163 | $CH_3$ | 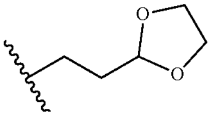 [SMILES: *CCC1OCCO1] | $Q_3$ | $CH_3$ | $CH_3$ | $CH_3$ | H | |
| 1-164 | $CH_3$ | 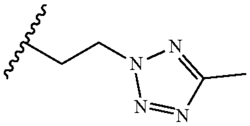 [SMILES: *CCn1nnc(C)n1] | $Q_3$ | $CH_3$ | $CH_3$ | $CH_3$ | H | |
| 1-165 | $CH_3$ | 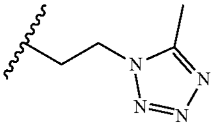 [SMILES: *CCn1nnnc1C] | $Q_3$ | $CH_3$ | 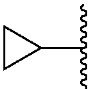 | $CH_3$ | H | |
| 1-166 | Cl | $CH_3$ | $Q_3$ | $CH_3$ | H | $CH_3$ | H | |
| 1-167 | Cl | $CH_3$ | $Q_3$ | $CH_3$ | $CH_3$ | $CH_3$ | H | yellow oil |
| 1-168 | Cl | $CH_3$ | $Q_3$ | $CH_2CH_3$ | H | $CH_3$ | H | yellow oil |
| 1-169 | Cl | $CH_3$ | $Q_3$ | $CH_2CH_3$ | $CH_3$ | $CH_3$ | H | |
| 1-170 | Cl | $CH_3$ | $Q_3$ | $CH_3$ | 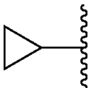 | $CH_3$ | H | |
| 1-171 | Cl | $CH_3$ | $Q_3$ | $CH_3$ | 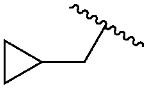 [SMILES: *CC1CC1] | $CH_3$ | H | |
| 1-172 | Cl | $CH_2CH_3$ | $Q_3$ | $CH_3$ | H | $CH_3$ | H | colorless oil |
| 1-173 | Cl | $CH_2CH_3$ | $Q_3$ | $CH_3$ | $CH_3$ | $CH_3$ | H | yellow oil |
| 1-174 | Cl | $CH_2CH_3$ | $Q_3$ | $CH_2CH_3$ | H | $CH_3$ | H | |
| 1-175 | Cl | $CH_2CH_3$ | $Q_3$ | $CH_2CH_3$ | $CH_3$ | $CH_3$ | H | white solid (142-144) |
| 1-176 | Cl | $CH_2CH_3$ | $Q_3$ | $CH_3$ | 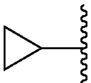 | $CH_3$ | H | |
| 1-177 | Cl | $CH_2CH_3$ | $Q_3$ | $CH_3$ | 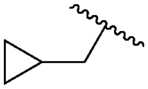 [SMILES: *CC1CC1] | $CH_3$ | H | |
| 1-178 | Cl | 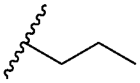 | $Q_3$ | $CH_3$ | $CH_3$ | $CH_3$ | H | yellow oil |

TABLE 1-continued

Structures and Physical Properties of Part of Compounds of Formula I

| Compound | $X_1$ | $Y_1$ | Q | $R_1$ | $R_2$ | $R_3$ | $R_5$ | Appearance (Melting Point ° C.) |
|---|---|---|---|---|---|---|---|---|
| 1-179 | Cl | 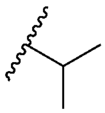 | $Q_3$ | $CH_3$ | $CH_3$ | $CH_3$ | H | yellow oil |
| 1-180 | Cl | 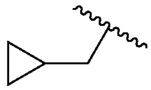 [SMILES: *CC1CC1] | $Q_3$ | $CH_3$ | H | $CH_3$ | H | |
| 1-181 | Cl | 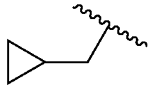 [SMILES: *CC1CC1] | $Q_3$ | $CH_3$ | $CH_3$ | $CH_3$ | H | yellow oil |
| 1-182 | Cl | 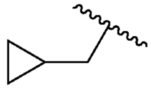 [SMILES: *CC1CC1] | $Q_3$ | $CH_2CH_3$ | H | $CH_3$ | H | |
| 1-183 | Cl | 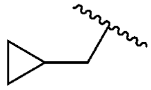 [SMILES: *CC1CC1] | $Q_3$ | $CH_2CH_3$ | $CH_3$ | $CH_3$ | H | |
| 1-184 | Cl | 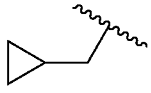 [SMILES: *CC1CC1] | $Q_3$ | $CH_3$ | 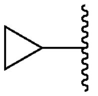 [SMILES: *C1CC1] | $CH_3$ | H | |
| 1-185 | Cl | 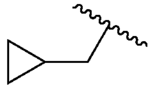 [SMILES: *CC1CC1] | $Q_3$ | $CH_3$ | 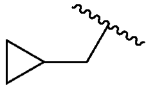 | $CH_3$ | H | |
| 1-186 | Cl | 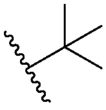 [SMILES: *C(C)(C)C] | $Q_3$ | $CH_3$ | $CH_3$ | $CH_3$ | H | |
| 1-187 | Cl | 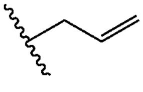 [SMILES: *CC=C] | $Q_3$ | $CH_3$ | $CH_3$ | $CH_3$ | H | yellow oil |
| 1-188 | Cl | 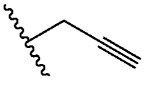 [SMILES: *CC#C] | $Q_3$ | $CH_3$ | $CH_3$ | $CH_3$ | H | yellow oil |
| 1-189 | Cl | 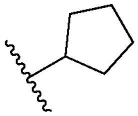 [SMILES: *C1CCCC1] | $Q_3$ | $CH_3$ | $CH_3$ | $CH_3$ | H | |
| 1-190 | Cl | 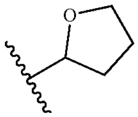 [SMILES: *C1CCCO1] | $Q_3$ | $CH_3$ | $CH_3$ | $CH_3$ | H | |
| 1-191 | Cl | 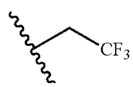 | $Q_3$ | $CH_3$ | $CH_3$ | $CH_3$ | H | |
| 1-192 | Cl | 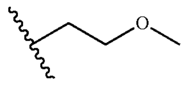 [SMILES: *CCOC] | $Q_3$ | $CH_3$ | H | $CH_3$ | H | yellow oil |

TABLE 1-continued

| Structures and Physical Properties of Part of Compounds of Formula I | | | | | | | | |
|---|---|---|---|---|---|---|---|---|
| Compound | $X_1$ | $Y_1$ | Q | $R_1$ | $R_2$ | $R_3$ | $R_5$ | Appearance (Melting Point ° C.) |
| 1-193 | Cl | 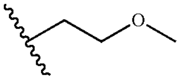 [SMILES: *CCOC] | $Q_3$ | $CH_3$ | $CH_3$ | $CH_3$ | H | colorless oil |
| 1-194 | Cl | 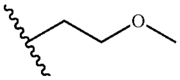 [SMILES: *CCOC] | $Q_3$ | $CH_2CH_3$ | H | $CH_3$ | H | yellow oil |
| 1-195 | Cl | 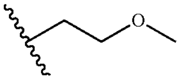 [SMILES: *CCOC] | $Q_3$ | $CH_2CH_3$ | $CH_3$ | $CH_3$ | H | yellow oil |
| 1-196 | Cl | 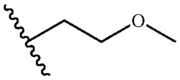 [SMILES: *CCOC] | $Q_3$ | $CH_3$ | 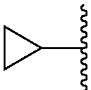 | $CH_3$ | H | |
| 1-197 | Cl | 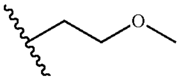 [SMILES: *CCOC] | $Q_3$ | $CH_3$ | 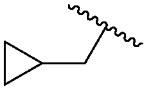 [SMILES: *CC1CC1] | $CH_3$ | H | |
| 1-198 | Cl | 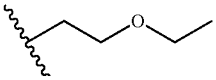 [SMILES: *CCOCC] | $Q_3$ | $CH_3$ | $CH_3$ | $CH_3$ | H | white solid (108-109) |
| 1-199 | Cl | 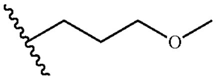 [SMILES: *CCCOC] | $Q_3$ | $CH_3$ | H | $CH_3$ | H | yellow oil |
| 1-200 | Cl | 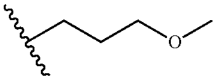 [SMILES: *CCCOC] | $Q_3$ | $CH_3$ | $CH_3$ | $CH_3$ | H | yellow oil |
| 1-201 | Cl | 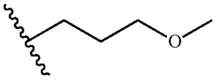 [SMILES: *CCCOC] | $Q_3$ | $CH_2CH_3$ | H | $CH_3$ | H | yellow oil |
| 1-202 | Cl | 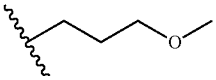 [SMILES: *CCCOC] | $Q_3$ | $CH_2CH_3$ | $CH_3$ | $CH_3$ | H | yellow oil |
| 1-203 | Cl | 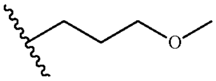 [SMILES: *CCCOC] | $Q_3$ | $CH_3$ | 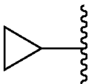 | $CH_3$ | H | |
| 1-204 | Cl | 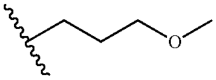 [SMILES: *CCCOC] | $Q_3$ | $CH_3$ | 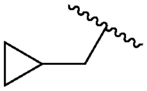 [SMILES: *CC1CC1] | $CH_3$ | H | |
| 1-205 | Cl | 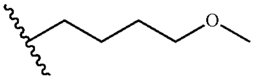 [SMILES: *CCCCOC] | $Q_3$ | $CH_3$ | $CH_3$ | $CH_3$ | H | red oil |
| 1-206 | Cl | 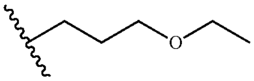 [SMILES: *CCCOCC] | $Q_3$ | $CH_3$ | $CH_3$ | $CH_3$ | H | |

TABLE 1-continued

| Compound | $X_1$ | $Y_1$ | Q | $R_1$ | $R_2$ | $R_3$ | $R_5$ | Appearance (Melting Point ° C.) |
|---|---|---|---|---|---|---|---|---|
| Structures and Physical Properties of Part of Compounds of Formula I | | | | | | | | |
| 1-207 | Cl | 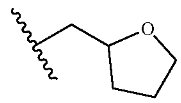 [SMILES: *CC1CCCO1] | $Q_3$ | $CH_3$ | $CH_3$ | $CH_3$ | H | |
| 1-208 | Cl | 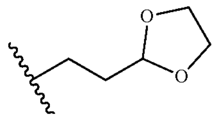 [SMILES: *CCC1OCCO1] | $Q_3$ | $CH_3$ | H | $CH_3$ | H | |
| 1-209 | Cl | 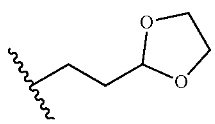 [SMILES: *CCC1OCCO1] | $Q_3$ | $CH_2CH_3$ | H | $CH_3$ | H | |
| 1-210 | Cl | 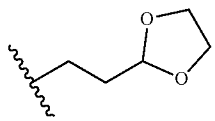 [SMILES: *CCC1OCCO1] | $Q_3$ | $CH_3$ | $CH_3$ | $CH_3$ | H | |
| 1-211 | Cl | 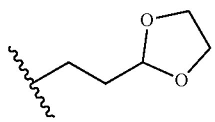 [SMILES: *CCC1OCCO1] | $Q_3$ | $CH_2CH_3$ | $CH_3$ | $CH_3$ | H | |
| 1-212 | Cl | 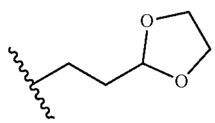 [SMILES: *CCC1OCCO1] | $Q_3$ | $CH_3$ | 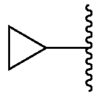 [SMILES: *C1CC1] | $CH_3$ | H | |
| 1-213 | Cl | 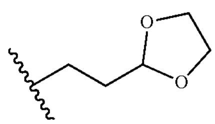 [SMILES: *CCC1OCCO1] | $Q_3$ | $CH_2CH_3$ | 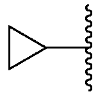 [SMILES: *C1CC1] | $CH_3$ | H | |
| 1-214 | Cl | 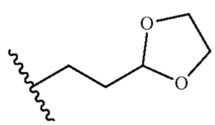 [SMILES: *CCC1OCCO1] | $Q_3$ | $CH_3$ | 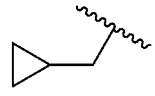 [SMILES: *CC1CC1] | $CH_3$ | H | |
| 1-215 | Cl | 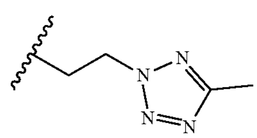 [SMILES: *CCn1nnc(C)n1] | $Q_3$ | $CH_3$ | $CH_3$ | $CH_3$ | H | |
| 1-216 | Cl | 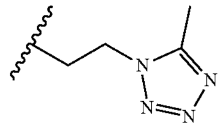 [SMILES: *CCn1nnnc1C] | $Q_3$ | $CH_3$ | 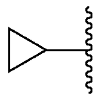 [SMILES: *C1CC1] | $CH_3$ | H | |

$^1$H NMR (300 MHz, $CDCl_3$) data of part of compounds is as follows:

Compound 1-1: 7.64 (d, 1H), 7.13 (d, 1H), 6.22 (s, 1H), 4.15 (q, 2H), 3.71 (s, 3H), 3.61 (s, 3H), 3.06 (s, 3H), 2.55 (s, 3H), 2.30 (s, 3H), 2.19 (s, 3H), 1.41 (t, 3H).

Compound 1-2: 7.96 (s, 1H), 7.71 (d, 1H), 7.19 (d, 1H), 6.38 (s, 1H), 4.18 (q, 2H), 3.78 (s, 3H), 3.73 (s, 3H), 3.11 (s, 3H), 2.33 (s, 3H), 2.24 (s, 3H), 1.44 (t, 3H).

Compound 1-3: 7.97 (s, 1H), 7.70 (d, 1H), 7.20 (d, 1H), 6.39 (s, 1H), 4.18 (q, 2H), 4.02 (q, 2H), 3.78 (s, 3H), 3.11 (s, 3H), 2.32 (s, 3H), 2.23 (s, 3H), 1.42-1.45 (m, 6H).

Compound 1-9: 7.93 (s, 1H), 7.69 (d, 1H), 7.16 (d, 1H), 6.36 (s, 1H), 4.16 (q, 2H), 3.87 (q, 2H), 103.71 (s, 3H), 3.11 (s, 3H), 2.30 (s, 3H), 2.20 (s, 3H), 1.39-1.43 (m, 6H).

Compound 1-10: 7.65 (d, 1H), 7.12 (d, 1H), 6.20 (s, 1H), 4.14 (q, 2H), 3.80 (q, 2H), 3.61 (s, 3H), 3.07 (s, 3H), 2.55 (s, 3H), 2.29 (s, 3H), 2.17 (s, 3H), 1.38-1.42 (m, 6H).

Compound 1-11: 7.96 (s, 1H), 7.71 (d, 1H), 7.18 (d, 1H), 6.38 (s, 1H), 4.17 (q, 2H), 4.01 (q, 2H), 3.90 (q, 2H), 3.13 (s, 3H), 2.32 (s, 3H), 2.21 (s, 3H), 1.40-1.45 (m, 9H).

Compound 1-12: 7.65 (d, 1H), 7.12 (d, 1H), 6.20 (s, 1H), 4.15 (q, 2H), 3.89 (q, 2H), 3.81 (q, 2H), 3.07 (s, 3H) 2.56 (s, 3H), 2.29 (s, 3H), 2.17 (s, 3H), 1.37-1.43 (m, 9H).

Compound 1-17: 7.65-7.67 (d, 1H), 7.11-7.13 (d, 1H), 6.21 (s, 1H), 4.13-4.16 (q, 2H), 3.69-3.71 (q, 2H), 3.61 (s, 3H), 3.07 (s, 3H) 2.55 (s, 3H), 2.29 (s, 3H), 2.17 (s, 3H), 1.79-1.83 (m, 2H), 1.40-1.43 (t, 3H), 1.03-1.05 (t, 3H).

TABLE 1-continued

| Structures and Physical Properties of Part of Compounds of Formula I | | | | | | | | |
|---|---|---|---|---|---|---|---|---|
| Compound | $X_1$ | $Y_1$ | Q | $R_1$ | $R_2$ | $R_3$ | $R_5$ | Appearance (Melting Point ° C.) |

Compound 1-18: 7.69 (d, 1H), 7.13 (d, 1H), 6.29 (s, 1H), 4.55-4.60 (m, 1H), 4.15 (q, 2H), 3.62 (s, 3H), 3.03 (s, 3H), 2.46 (s, 3H), 2.29 (s, 3H), 2.21 (s, 3H), 1.43 (t, 3H), 1.26 (d, 6H).
Compound 1-19: 7.94 (s, 1H), 7.71 (d, 1H), 7.18 (d, 1H), 6.37 (s, 1H), 4.17 (q, 2H), 3.72 (s, 3H), 3.66 (d, 2H), 3.17 (s, 3H), 2.31 (s, 3H), 2.22 (s, 3H), 1.44 (t, 3H), 1.30-1.36 (m, 1H), 0.62-0.65 (m, 2H), 0.37-0.40 (m, 2H).
Compound 1-20: 7.64-7.66 (d, 1H), 7.10-7.12 (d, 1H), 6.19 (s, 1H), 4.10-4.14 (q, 2H), 3.60 (s, 3H), 3.55-3.56 (q, 2H), 3.10 (s, 3H), 2.53 (s, 3H), 2.27 (s, 3H), 2.17 (s, 3H), 1.40-1.42 (t, 3H), 1.25-1.33 (m, 1H), 0.60-0.63 (t, 2H) , 0.35-0.37 (t, 2H).
Compound 1-26: 7.67 (d, 1H), 7.14 (d, 1H), 6.22 (s, 1H), 6.05-6.11 (m, 1H), 5.43 (d, 1H), 5.29 (d, 1H), 4.25 (d, 2H), 4.14 (q, 2H), 3.61 (s, 3H), 3.08 (s, 3H), 2.56 (s, 3H), 2.29 (s, 3H), 2.18 (s, 3H), 1.41 (t, 3H).
Compound 1-27: 7.65 (d, 1H), 7.17 (d, 1H), 6.22 (s, 1H), 4.40 (d, 2H), 4.15 (q, 2H), 3.61 (s, 3H), 3.10 (s, 3H), 2.62 (t, 1H), 2.56 (s, 3H), 2.30 (s, 3H), 2.24 (s, 3H), 1.42 (t, 3H).
Compound 1-30: 7.67 (d, 1H), 7.20 (d, 1H), 6.18 (s, 1H), 4.10-4.11 (m, 4H), 3.57 (s, 3H), 3.06 (s, 3H), 2.53 (s, 3H), 2.27 (s, 3H), 2.17 (s, 3H), 1.39 (t, 3H).
Compound 1-31: 7.69 (s, 1H), 7.72-7.73 (d, 1H), 7.21-7.22 (d, 1H), 6.39 (s, 1H), 4.16-4.20 (m, 2H), 4.02-4.03 (t, 2H), 3.73-3.75 (t, 2H), 3.16 (s, 3H), 2.32 (s, 3H), 2.26 (s, 3H), 1.43-1.46 (t, 3H).
Compound 1-32: 7.94 (s, 1H), 7.71 (d, 1H), 7.21 (d, 1H), 6.39 (s, 1H), 4.18 (q, 2H), 3.99-4.03 (m, 4H), 3.74 (t, 2H), 3.44 (s, 3H), 3.15 (s, 3H), 2.31 (s, 3H), 2.25 (s, 3H), 1.41-1.45 (m, 6H).
Compound 1-33: 7.66-7.67 (d, 1H), 7.14-7.15 (d, 1H), 6.22 (s, 1H), 4.12-4.14 (q, 2H), 3.91-3.93 (t, 2H), 3.71-3.72 (t, 2H), 3.61 (s, 3H), 3.17 (s, 3H) , 3.10 (s, 3H), 2.54 (s, 3H), 2.29 (s, 3H), 2.21 (s, 3H), 1.40-1.43 (t, 3H).
Compound 1-34: 7.66-7.67 (d, 1H), 7.15-7.16 (d, 1H), 6.23 (s, 1H), 4.22-4.27 (m, 1H), 4.13-4.17 (m, 2H), 3.93-3.94 (t, 2H), 3.72-3.73 (t, 2H), 3.44 (s, 3H), 3.11 (s, 3H), 2.56 (s, 3H), 2.30 (s, 3H), 2.21 (s, 3H), 1.44 (s, 6H), 1.39-1.42 (t, 3H).
Compound 1-35: 7.66-7.68 (d, 1H), 7.18-7.19 (d, 1H), 6.24 (s, 1H), 4.15-4.17 (t, 2H), 3.94-3.96 (t, 2H), 3.74 (s, 3H), 3.72-3. 73 (q, 2H), 3.44 (s, 3H), 3.12 (s, 3H), 2.30 (s, 3H), 2.23 (s, 3H), 1.41-1.43 (t, 3H).
Compound 1-36: 7.65-7.66 (d, 1H), 7.14-7.15 (d, 1H), 6.20 (s, 1H), 4.13-4.16 (t, 2H), 3.92-3.94 (t, 2H), 3.71-3. 72 (q, 2H), 3.62 (s, 3H), 3.44 (s, 3H), 3.10 (s, 3H), 2.99-3.01 (q, 2H), 2.29 (s, 3H), 2.20 (s, 3H), 1.40-1.43 (t, 3H), 1.31-1.34 (t, 3H).
Compound 1-37: 7.66-7.67 (d, 1H), 7.15-7.16 (d, 1H), 6.23 (s, 1H), 4.14-4.16 (t, 2H), 3.88-3.95 (m, 4H), 3.71-3. 73 (t, 2H), 3.44 (s, 3H), 3.44 (s, 3H), 3.11 (s, 3H), 2.256 (s, 3H), 2.30 (s, 3H), 2.22 (s, 3H), 1.38-1.40 (t, 3H), 1.25-1.27 (t, 3H).
Compound 1-38: 7.65 (d, 1H), 7.14 (d, 1H), 6.17 (s, 1H), 4.12 (q, 2H), 3.93 (t, 2H), 3.72 (t, 2H), 3.65 (m, 1H), 3.61 (s, 3H), 3.44 (s, 3H), 3.10 (s, 3H), 2.29 (s, 3H), 2.20 (s, 3H), 1.42 (t, 3H), 1.35 (d, 6H).
Compound 1-39: 7.67 (d, 1H), 7.18 (d, 1H), 6.22 (s, 1H), 4.14 (q, 2H), 3.94 (t, 2H), 3.72 (t, 2H), 3.56 (s, 3H), 3.44 (s, 3H), 3.11 (s, 3H), 2.62 (m, 1H), 2.29 (s, 3H), 2.24 (s, 3H), 1.42 (t, 3H), 0.97-1.03 (m, 4H).
Compound 1-41: 7.64 (d, 1H), 7.14 (d, 1H), 6.18 (s, 1H), 4.10 (q, 2H), 3.92 (t, 2H), 3.70 (t, 2H), 3.62 (s, 3H), 3.43 (s, 3H), 3.09 (s, 3H), 2.88 (d, 2H), 2.28 (s, 3H), 2.19 (s, 3H), 1.40 (t, 3H), 1.20-1.24 (m, 1H), 0.49-0.52 (m, 2H), 0.26-0.28 (m, 2H).
Compound 1-44: 7.65-7.66 (d, 1H), 7.13-7.14 (d, 1H), 6.21 (s, 1H), 4.11-4.14 (m, 2H), 3.82-3.84 (t, 2H), 3.71-3.73 (t, 2H), 3.60 (s, 3H), 3.56-3.59 (q, 2H), 3.10 (s, 3H), 2.54 (s, 3H) 2.29 (s, 3H), 2.21 (s, 3H), 1.40-1.42 (t, 3H), 1.24-1.22 (t, 3H).
Compound 1-48: 7.64-7.65 (d, 1H), 7.12-7.13 (d, 1H), 6.22 (s, 1H), 4.13-4.17 (q, 2H), 3.84-3.86 (t, 2H), 3.61 (s, 3H), 3.55-3.57 (t, 2H), 3.06 (s, 3H), 2.55 (s, 3H), 2.29 (s, 3H), 2.18 (s, 3H), 2.03-2.06 (m, 2H), 1.40-1 43 (t, 3H).
Compound 1-53: 7.64-7.65 (d, 1H), 7.11-7.12 (d, 1H), 6.21 (s, 1H), 4.12-4.14 (q, 2H), 3.76-3.78 (t, 2H), 3.61 (s, 3H), 3.43-3.45 (t, 2H), 3.06 (s, 3H), 2.54 (s, 3H), 2.28 (s, 3H), 2.16 (s, 3H), 1.82-1.86 (m, 2H), 1.72-1.77 (m, 2H), 1.40-1.42 (t, 3H).
Compound 1-55: 7.66 (d, 1H), 7.14 (d, 1H), 6.23 (s, 1H), 4.26-4.31 (m, 1H), 4.15 (q, 2H), 3.89-3.93 (m, 1H), 3.82-3.86 (m, 1H), 3.77-3.79 (m, 1H), 3.71-3.74 (m ,1H), 3.61 (s, 3H), 3.11 (s, 3H), 2.54 (s, 3H), 2.29 (s, 3H), 2.21 (s, 3H), 2.03-2.08 (m, 1H), 1.91-1.96 (m, 2H), 1.67-1.73 (m, 1H), 1.42 (t, 3H).
Compound 1-60: 7.66 (d, 1H), 7.16 (d, 1H), 6.25 (d, 1H), 4.15 (q, 2H), 3.89 (s, 3H), 3.70 (q, 2H), 3.06 (s, 3H), 2.54 (s, 3H), 2.29 (d, 3H), 1.40 (t, 3H), 1.22 (t, 3H).
Compound 1-65: 7.94 (s, 1H), 7.74 (d, 1H), 7.19 (d, 1H), 6.39 (s, 1H), 4.12-4.07 (m, 2H), 3.71 (s, 3H), 3.13 (s, 3H), 2.31 (s, 3H), 1.42 (m, 3H).
Compound 1-66: 7.67 (d, 1H), 7.14 (d, 1H), 6.24 (s, 1H), 4.14-4.19 (m, 4H), 3.60 (s, 3H), 3.08 (s, 3H), 2.54 (s, 3H), 2.28 (s, 3H), 1.44-1.50 (m, 6H).
Compound 1-67: 7.74 (d, 1H), 7.20 (d, 1H), 6.40 (s, 1H), 4.17 (t, 2H), 4.01 (t, 2H), 3.71 (s, 3H), 3.13 (s, 3H), 2.31 (s, 3H), 1.44-1.49 (m, 6H).
Compound 1-68: 7.68 (d, 1H), 7.15 (d, 1H), 6.26 (s, 1H), 4.16 (q, 2H), 4.09 (q, 2H), 3.91 (q, 2H), 3.10 (s, 3H), 2.56 (s, 3H), 2.30 (s, 3H), 1.45 (t, 3H), 1.42 (t, 3H), 1.40 (t, 3H).
Compound 1-73: 7.68 (d, 1H), 7.14 (d, 1H), 6.25 (d, 1H), 4.14 (q, 2H), 3.96 (s, 2H), 3.61 (s, 3H), 3.08 (s, 3H), 2.54 (s, 3H), 2.28 (s, 3H), 1.88-1.82 (m, 2H), 1.41 (t, 3H), 1.04 (t, 3H).
Compound 1-74: 7.70 (d, 1H), 7.12 (d, 1H), 6.30 (d, 1H), 5.10-5.12 (m, 1H), 4.15 (q, 2H), 3.62 (s, 3H), 3.06 (s, 3H), 2.48 (s, 3H), 2.29 (s, 3H), 1.43 (t, 3H), 1.33 (d, 6H).
Compound 1-76: 7.68 (d, 1H), 7.14 (d, 1H), 6.24 (d, 1H), 4.13 (q, 2H), 3.81 (s, 2H), 3.60 (s, 3H), 3.13 (s, 3H), 2.53 (s, 3H), 2.27 (s, 3H), 1.60-1.66 (m, 1H), 1.40 (t, 3H), 0.68-0.60 (m, 2H), 0.44-0.37 (m, 2H).
Compound 1-82: 7.69 (d, 1H), 7.17 (d, 1H), 6.26 (d, 1H), 6.12 (t, 1H), 5.44 (q, 1H), 5.32 (q, 1H), 4.48 (d, 2H), 4.14 (q, 2H), 3.61 (s, 3H), 3.08 (s, 3H), 2.55 (s, 3H), 2.29 (s, 3H), 1.40 (t, 3H).
Compound 1-83: 7.69 (d, 1H), 7.21 (d, 1H), 6.26 (d, 1H), 4.65-4.59 (m, 2H), 4.15 (q, 2H), 3.61 (s, 3H), 3.13 (s, 3H), 2.63 (t, 1H), 2.55 (s, 3H), 2.30 (s, 3H), 1.42 (t, 3H).
Compound 1-87: 7.75 (d, 1H), 7.21 (d, 1H), 6.40 (s, 1H), 4.23 (t, 2H), 4.16 (q, 2H), 3.80-3.75 (m, 2H), 3.71 (s, 3H), 3.43 (s, 3H), 3.17 (s, 3H), 2.30 (s, 3H), 1.42 (t, 3H).
Compound 1-88: 7.69 (d, 1H), 7.17 (d, 1H), 6.26 (d, 1H), 4.16 (m, 4H), 3.77 (t, 2H), 3.61 (s, 3H), 3.43 (s, 3H), 3.13 (s, 3H), 2.54 (s, 3H), 2.29 (s, 3H), 1.42 (m, 3H).
Compound 1-89: 7.92 (d, 1H), 7.75 (d, 1H), 7.21 (d, 1H), 6.40 (d, 1H), 4.23 (q, 2H), 4.15 (q, 2H), 3.99 (q, 2H), 3.77 (d, 2H), 3.42 (s, 3H), 3.16 (s, 3H), 2.30 (s, 3H), 1.40-1.44 (m, 6H).
Compound 1-90: 7.69 (d, 1H), 7.17 (d, 1H), 6.27 (s, 1H), 4.19 (brs, 2H), 4.16 (q, 2H), 3.91 (q, 2H), 3.78 (t, 2H), 3.44 (s, 3H), 3.13 (s, 3H), 2.55 (s, 3H), 2.29 (s, 3H), 1.42 (t, 3H), 1.39 (t, 3H).
Compound 1-93: 7.69 (d, 1H), 7.17 (d, 1H), 6.26 (s, 1H), 4.13-4.21 (m, 4H), 3.81 (t, 2H), 3.62 (s, 3H), 3.59 (q, 2H), 3.14 (s, 3H), 2.54 (s, 3H), 2.29 (s, 3H), 1.42 (t, 3H), 1.23 (t, 3H).
Compound 1-94: 7.96 (s, 1H), 7.74 (d, 1H), 7.19 (d, 1H), 6.40 (s, 1H), 4.15-4.19 (m, 4H), 3.72 (s, 3H), 3.58 (t, 2H), 3.36 (s, 3H), 3.12 (s, 3H), 2.31 (s, 3H), 2.09-2.14 (m, 2H), 1.43 (t, 3H).
Compound 1-95: 7.67 (d, 1H), 7.14 (d, 1H), 6.26 (s, 1H), 4.06-4.16 (m, 4H), 3.61 (s, 3H), 3.57 (t, 2H), 3.36 (s, 3H), 3.08 (s, 3H), 2.54 (s, 3H), 2.29 (s, 3H), 2.07-2.12 (m, 2H), 1.41 (t, 3H).
Compound 1-96: 7.96 (s, 1H), 7.73 (d, 1H), 7.19 (d, 1H), 6.40 (s, 1H), 4.14-4.19 (m, 4H), 4.00 (q, 2H), 3.57 (t, 2H), 3.35 (s, 3H), 3.12 (s, 3H), 2.30 (s, 3H), 2.08-2.13 (m, 2H), 1.40-1.44 (m, 6H).
Compound 1-100: 7.67 (d, 1H), 7.14 (d, 1H), 6.25 (s, 1H), 4.16 (q, 2H), 4.03 (t, 2H), 3.61 (s, 3H), 3.45 (t, 2H), 3.34 (s, 3H), 3.07 (s, 3H), 2.54 (s, 3H), 2.29 (s, 3H), 1.91 (m, 2H), 1.78 (m, 2H), 1.41 (t, 3H).
Compound 1-102: 7.71 (d, 1H), 7.17 (d, 1H), 6.27 (s, 1H), 4.32-4.37 (m, 1H), 4.16 (q, 2H), 4.08 (t, 1H), 3.89-3.94 (m, 2H), 3.82-3.86 (m, 1H), 3.62 (s, 3H), 3.15 (s, 3H), 2.55 (s, 3H), 2.29 (s, 3H), 2.03-2.09 (m, 1H), 1.91-1.98 (m, 2H), 1.74-1.81 (m, 1H), 1.42 (t, 3H).
Compound 1-112: 7.64 (d, 1H), 7.07 (d, 1H), 6.31 (s, 1H), 4.28 (q, 2H), 3.70 (s, 3H), 3.57 (s, 3H), 2.91 (s, 3H), 2.37 (s, 3H), 2.19 (s, 3H), 2.18 (s, 3H), 1.27 (t, 3H).
Compound 1-113: 7.83 (d, 1H), 7.74 (s, 1H), 7.28 (d, 1H), 6.72 (s, 1H), 4.48 (q, 2H), 3.90 (s, 3H), 3.79 (s, 3H), 3.16 (s, 3H), 2.33 (s, 3H), 2.31 (s, 3H), 1.42 (t, 3H).
Compound 1-114: 7.83 (d, 1H), 7.72 (s, 1H), 7.27 (d, 1H), 6.72 (s, 1H), 4.47 (q, 2H), 4.08 (q, 2H), 3.89 (s, 3H), 3.15 (s, 3H), 2.32 (s, 3H), 2.29 (s, 3H), 1.47 (t, 3H), 1.41 (t, 3H).
Compound 1-118: 7.81 (d, 1H), 7.71 (s, 1H), 7.23 (d, 1H), 6.69 (s, 1H), 4.45 (q, 2H), 4.01 (q, 2H), 3.76 (s, 3H), 3.15 (s, 3H), 2.30 (s, 3H), 2.26 (s, 3H), 1.44 (t, 3H), 1.40 (t, 3H).
Compound 1-119: 7.74 (d, 1H), 7.12 (d, 1H), 6.36 (s, 1H), 4.35 (q, 2H), 3.89 (q, 2H), 3.63 (s, 3H), 3.01 (s, 3H), 2.44 (s, 3H), 2.26 (s, 3H), 2.23 (s, 3H), 1.41 (t, 3H), 1.34 (t, 3H).
Compound 1-120: 7.83 (d, 1H), 7.71 (s, 1H), 7.25 (d, 1H), 6.72 (s, 1H), 4.46 (q, 2H), 4.08 (q, 2H), 4.03 (q, 2H), 3.16 (s, 3H), 2.31 (s, 3H), 2.27 (s, 3H), 1.44-1.47 (m, 6H), 1.40 (t, 3H).
Compound 1-121: 7.74 (d, 1H), 7.12 (d, 1H), 6.39 (s, 1H), 4.36 (q, 2H), 3.87-3.94 (m, 4H), 3.01 (s, 3H), 2.43 (s, 3H), 2.27 (s, 3H), 2.23 (s, 3H), 1.39-1.43 (m, 6H), 1.34 (t, 3H).
Compound 1-126: 7.82 (d, 1H), 7.71 (s, 1H), 7.23 (d, 1H), 6.68 (s, 1H), 4.46 (q, 2H), 3.79 (q, 2H), 3.77 (s, 3H), 3.20 (s, 3H), 2.31 (s, 3H), 2.27 (s, 3H), 1.41 (t, 3H), 1.34-1.38 (m, 1H), 0.62-0.65 (m, 2H), 0.39-0.42 (m, 2H).
Compound 1-127: 7.74 (d, 1H), 7.12 (d, 1H), 6.35 (s, 1H), 4.36 (q, 2H), 3.63-3.66 (m, 5H), 3.07 (s, 3H), 2.43 (s, 3H), 2.26 (s, 3H), 2.23 (s, 3H), 1.36 (t, 3H), 1.29-1.33 (m, 1H), 0.60-0.64 (m, 2H), 0.37-0.40 (m, 2H).
Compound 1-128: 7.84 (d, 1H), 7.71 (s, 1H), 7.24 (d, 1H), 6.71 (s, 1H), 4.47 (q, 2H), 4.08 (q, 2H), 3.80 (d, 2H), 3.21 (s, 3H), 2.32 (s, 3H), 2.28 (s, 3H), 1.46 (t, 3H), 1.41 (t, 3H), 1.34-1.37 (m, 1H), 0.62-0.65 (m, 2H), 0.40-0.42 (m, 2H).
Compound 1-138: 7.85 (d, 1H), 7.69 (s, 1H), 7.26 (d, 1H), 6.71 (s, 1H), 4.48 (q, 2H), 4.14 (t, 2H), 3.77-3.79 (m, 5H), 3.46 (s, 3H), 3.21 (s, 3H), 2.32 (s, 3H), 2.31 (s, 3H), 1.42 (t, 3H).
Compound 1-139: 7.84-7.85 (d, 1H), 7.69 (s, 1H), 7.26-7.27 (d, 1H), 6.72 (s, 1H), 4.46-4.50 (q, 2H), 4.13-4.15 (t, 2H), 4.06-4.10 (t, 2H), 3.77-3.78 (t, 2H), 3.45 (s, 3H), 3.21 (s, 3H), 2.31 (s, 6H), 1.45-1.48 (t, 3H), 1.40-1.43 (t, 3H).
Compound 1-140: 7.76 (d, 1H), 7.14 (d, 1H), 6.37 (s, 1H), 4.37 (q, 2H), 3.99 (t, 2H), 3.73 (t, 2H), 3.64 (s, 3H), 3.44 (s, 3H), 3.07 (s, 3H), 2.42 (s, 3H), 2.27 (d, 6H), 1.37 (t, 3H).
Compound 1-144: 7.76 (d, 1H), 7.14 (d, 1H), 6.40 (s, 1H), 4.38 (q, 2H), 3.99 (t, 2H), 3.93 (q, 2H), 3.73 (t, 2H), 3.44 (s, 3H), 3.07 (s, 3H), 2.40 (s, 3H), 2.27 (s, 3H), 2.26 (s, 3H), 1.41 (t, 3H), 1.36 (t, 3H).
Compound 1-148: 7.74 (d, 1H), 7.16 (d, 1H), 6.29 (s, 1H), 4.36 (q, 2H), 3.95 (t, 2H), 3.72 (t, 2H), 3.65 (s, 3H), 3.44 (s, 3H), 3.04 (s, 3H), 2.81 (d, 2H), 2.27 (d, 6H), 1.35 (t, 3H), 1.15-1.21 (m, 1H), 0.49-0.52 (m, 2H), 0.23-0.26 (m, 2H).

TABLE 1-continued

Structures and Physical Properties of Part of Compounds of Formula I

| Compound | $X_1$ | $Y_1$ | Q | $R_1$ | $R_2$ | $R_3$ | $R_5$ | Appearance (Melting Point ° C.) |
|---|---|---|---|---|---|---|---|---|
| Compound 1-167: 7.78 (d, 1H), 7.15 (d, 1H), 6.40 (s, 1H), 4.38 (q, 2H), 3.92 (s, 3H), 3.63 (s, 3H), 3.01 (s, 3H), 2.45 (s, 3H), 2.25 (s, 3H), 1.35 (t, 3H). | | | | | | | | |
| Compound 1-168: 7.74 (d, 1H), 7.20 (d, 1H), 6.40 (s, 1H), 4.24-3.94 (m, 6H), 3.13 (s, 3H), 2.31 (s, 3H), 1.51-1.36 (m, 9H). | | | | | | | | |
| Compound 1-172: 7.88 (d, 1H), 7.73 (s, 1H), 7.23 (d, 1H), 6.69 (s, 1H), 4.47 (q, 2H), 4.22 (q, 2H), 3.76 (s, 3H), 3.16 (s, 3H), 2.30 (s, 3H), 1.48 (t, 3H), 1.41 (t, 3H). | | | | | | | | |
| Compound 1-173: 7.79 (d, 1H), 7.13 (d, 1H), 6.40 (s, 1H), 4.38 (q, 2H), 4.10 (q, 2H), 3.62 (s, 3H), 3.02 (s, 3H), 2.44 (s, 3H), 2.25 (s, 3H), 1.44 (t, 3H), 1.35 (t, 3H). | | | | | | | | |
| Compound 1-175: 7.79 (d, 1H), 7.14 (d, 1H), 6.45 (s, 1H), 4.39 (q, 2H), 4.14 (q, 2H), 3.92 (q, 2H), 3.04 (s, 3H), 2.45 (s, 3H), 2.27 (s, 3H), 1.46 (t, 3H), 1.42 (t, 3H), 1.37 (t, 3H). | | | | | | | | |
| Compound 1-178: 7.75 (d, 1H), 7.09 (d, 1H), 6.35 (s, 1H), 4.34 (q, 2H), 3.80 (d, 2H), 3.58 (s, 3H), 3.04 (s, 3H), 2.40 (s, 3H), 2.21 (s, 3H), 1.32 (t, 3H), 0.63-0.55 (m, 2H), 0.36 (t, 2H). | | | | | | | | |
| Compound 1-179: 7.82 (d, 1H), 7.10-7.07 (m, 1H), 6.50-6.48 (m, 1H), 5.19 (m, 1H), 4.38 (q, 2H), 3.62 (s, 3H), 2.97 (s, 3H), 2.39 (s, 3H), 2.25 (s, 3H), 1.35 (t, 3H), 1.31 (d, 6H). | | | | | | | | |
| Compound 1-181: 7.78 (d, 1H), 7.12 (d, 1H), 5.27 (s, 1H), 4.36 (q, 2H), 3.98 (t, 2H), 3.61 (s, 3H), 3.01 (s, 3H), 2.43 (s, 3H), 2.24 (s, 3H), 1.83-1.87 (m, 1H), 1.34 (t, 3H), 0.70-0.64 (m, 2H), 0.46-0.42 (m, 2H). | | | | | | | | |
| Compound 1-187: 7.78 (d, 1H), 7.14 (d, 1H), 6.39 (s, 1H), 6.15-6.06 (m, 1H), 5.44 (q, 1H), 5.31 (q, 1H), 4.53-4.49 (m, 2H), 4.36 (q, 2H), 3.61 (s, 3H), 3.01 (s, 3H), 2.43 (s, 3H), 2.23 (s, 3H), 1.33 (t, 3H). | | | | | | | | |
| Compound 1-192: 7.91-7.89 (m, 1H), 7.70 (s, 1H), 7.25 (d, 1H), 6.72 (d, 1H), 4.47 (q, 2H), 4.32 (d, 2H), 3.82-3.79 (m, 2H), 3.76 (s, 3H), 3.44 (s, 3H), 3.21 (s, 3H), 2.30 (s, 3H), 1.40 (t, 3H). | | | | | | | | |
| Compound 1-193: 7.81 (d, 1H), 7.15 (d, 1H), 6.41 (s, 1H), 4.38 (q, 2H), 4.23-4.17 (m, 2H), 3.80-3.77 (m, 2H), 3.62 (s, 3H), 3.44 (s, 3H), 3.09 (s, 3H), 2.42 (s, 3H), 2.25 (s, 3H), 1.36 (t, 3H). | | | | | | | | |
| Compound 1-194: 7.87 (d, 1H), 7.68 (s, 1H), 7.25 (s, 1H), 6.70 (d, 1H), 4.45 (q, 2H), 4.33-4.29 (m, 2H), 4.04 (q, 2H), 3.80-3.76 (m, 2H), 3.42 (s, 3H), 3.20 (s, 3H), 2.27 (s, 3H), 1.43 (t, 3H), 1.40-1.37 (m, 3H). | | | | | | | | |
| Compound 1-195: 7.81 (d, 1H), 7.16 (d, 1H), 6.46 (s, 1H), 4.39 (q, 2H), 4.22 (t, 2H), 3.91 (q, 2H), 3.78 (t, 2H), 3.44 (s, 3H), 3.09 (s, 3H), 2.42 (s, 3H), 2.26 (s, 3H), 1.41 (t, 3H), 1.36 (t, 3H). | | | | | | | | |
| Compound 1-198: 7.81 (d, 1H), 7.14 (d, 1H), 6.42 (s, 1H), 4.38 (q, 2H), 4.21 (t, 2H), 3.81 (t, 2H), 3.63 (s, 3H), 3.59 (q, 2H), 3.10 (s, 3H), 2.43 (s, 3H), 2.26 (s, 3H), 1.36 (t, 3H), 1.23 (t, 3H). | | | | | | | | |
| Compound 1-199: 7.89 (d, 1H), 7.73 (s, 1H), 7.25 (d, 1H), 6.69 (s, 1H), 4.48 (q, 2H), 4.26 (t, 2H), 3.77 (s, 3H), 3.59 (t, 2H), 3.36 (s, 3H), 3.16 (s, 3H), 2.31 (s, 3H), 2.12-2.18 (m, 2H), 1.42 (t, 3H). | | | | | | | | |
| Compound 1-200: 7.79 (d, 1H), 7.14 (d, 1H), 6.40 (s, 1H), 4.38 (q, 2H), 4.14 (t, 2H), 3.63 (s, 3H), 3.57 (t, 2H), 3.36 (s, 3H), 3.03 (s, 3H), 2.45 (s, 3H), 2.26 (s, 3H), 2.12 (m, 2H), 1.37 (t, 3H). | | | | | | | | |
| Compound 1-201: 7.88 (d, 1H), 7.73 (s, 1H), 7.25 (d, 1H), 6.71 (s, 1H), 4.48 (q, 2H), 4.26 (t, 2H), 4.07 (q, 2H), 3.59 (t, 2H), 3.35 (s, 3H), 3.16 (s, 3H), 2.30 (s, 3H), 2.12-2.17 (m, 2H), 1.46 (t, 3H), 1.41 (t, 3H). | | | | | | | | |
| Compound 1-202: 7.79 (d, 1H), 7.14 (d, 1H), 6.43 (s, 1H), 4.39 (q, 2H), 4.15 (t, 2H), 3.91 (q, 2H), 3.57 (t, 2H), 3.36 (s, 3H), 3.03 (s, 3H), 2.44 (s, 3H), 2.26 (s, 3H), 2.09-2.14 (m, 2H), 1.41 (t, 3H), 1.36 (t, 3H). | | | | | | | | |
| Compound 1-205: 7.79 (d, 1H), 7.14 (d, 1H), 6.40 (s, 1H), 4.38 (q, 2H), 4.06 (t, 2H), 3.63 (s, 3H), 3.45 (t, 2H), 3.35 (s, 3H), 3.02 (s, 3H), 2.45 (s, 3H), 2.26 (s, 3H), 1.89 (m, 2H), 1.75 (m, 2H), 1.36 (t, 3H). | | | | | | | | |

Biometric Test Examples

Example 5 Determination of Herbicidal Activity

Seeds of broadleaf weeds (*Zinnia elegans* Jacq. and *Abutilon theophrasti* Medic.) or grass weeds (*Setaria glauca* (L.) Beauv. and *Echinochloa crusgalli* (L.) Beauv.) were respectively sown in a paper cup having a diameter of 7 cm and containing nutrient soil. After sowing, the seeds were covered with 1 cm of soil, the soil was pressed and watered, and then the seeds were cultivated in a greenhouse according to a conventional method, and stems and leaves were sprayed after 2-3 leaf stage of the weeds.

The compounds of the present invention were dissolved in acetone, and then diluted with 0.1% aqueous solution of Tween 80 to form the test liquid. According to the design dose of the test, spray treatment was carried out by track sprayer (Engineer Research Ltd., pressure 1.95 kg/cm$^2$, volume 500 L/hm$^2$, track speed 1.48 km/h). The test was repeated for three times. The test material was treated and then placed in an operation hall. The medicinal liquid was naturally dried in the shade, and then was placed in a greenhouse and managed according to the conventional method. The response of the weeds to the drug was visually observed and recorded. After treatment, the state of growth of the respective weeds were visually observed regularly to determine the growth inhibition rate (%) in accordance with the following evaluation standard.

Growth inhibition rate (%): 0=no discernible action: 100=all weeds dead or not emerged.

The test results show that the compounds of the formula I generally have high growth inhibition rates on various weeds. Part of the test compounds, such as compounds 1-1, 1-10, 1-17, 1-18, 1-20, 1-26, 1-27, 1-30, 1-31, 1-32, 1-33, 1-34, 1-36, 1-37, 1-38, 1-39, 1-44, 1-48, 1-53, 1-55, 1-60, 1-65, 1-66, 1-67, 1-74, 1-76, 1-82, 1-83, 1-88, 1-93, 1-95, 1-100, 1-102, 1-139, 1-140, 1-167, 1-168, 1-173, 1-178, 1-179, 1-181, 1-187, 1-193, 1-198, 1-200 and 1-205, have good growth inhibition rates on *Zinnia elegans* Jacq., *Abutilon theophrasti* Medic., *Setaria glauca* (L.) Beauv. or *Echinochloa crusgalli* (L.) Beauv. At the application dose of 600 g a.i./hm$^2$, the growth inhibition rates are greater than or equal to 90%.

According to the above test method, part of the compounds having general formula I and KC1 and KC2 were selected for activity test against *Setaria glauca* (L.) Beauv. The results were shown in Table 2.

TABLE 2

The test results of part of the compounds having general Formula I and KC1, KC2 against *Setaria glauca* (L.) Beauv. (Post-emergence treatment, growth inhibition rate %)

| | dose g a.i./hm$^2$ | | |
|---|---|---|---|
| Compound | 600 | 150 | 37.5 |
| 1-20 | 100 | 100 | 65 |
| 1-26 | 100 | 100 | 75 |
| 1-32 | 100 | 100 | 90 |
| 1-33 | 100 | 100 | 70 |
| 1-34 | 100 | 100 | 65 |
| 1-36 | 100 | 100 | 70 |
| 1-37 | 100 | 100 | 100 |
| 1-44 | 100 | 100 | 70 |
| 1-139 | 100 | 100 | 80 |
| 1-140 | 100 | 100 | 80 |
| KC1 | 60 | 45 | / |
| KC2 | 60 | 50 | / |

"/" in the table indicates no test.

According to the above test method, compound 1-32 and KC3 were selected for parallel tests against *Zinnia elegans* Jacq., *Abutilon theophrasti* Medic. and *Setaria glauca* (L.) Beauv. The results were shown in Table 3.

TABLE 3

The test results of compound 1-32 and KC3 against *Zinnia elegans* Jacq., *Abutilon theophrasti* Medic. and *Setaria glauca* (L.) Beauv. (Post-emergence treatment, growth inhibition rate %)

| | dose g a.i./hm$^2$ | | | | | |
|---|---|---|---|---|---|---|
| | *Zinnia elegans* Jacq. | | *Abutilon theophrasti* Medic. | | *Setaria glauca* (L.) Beauv. | |
| Compound | 75 | 37.5 | 75 | 37.5 | 75 | 37.5 |
| 1-32 | 100 | 100 | 100 | 100 | 100 | 90 |
| KC3 | 50 | 40 | 95 | 30 | 70 | 60 |

To sum up, the pyrazole carboxylate ester compounds of the present invention have excellent herbicidal activity, also have high herbicidal activity at a lower dosage, which are safe for crops and can be used for controlling various weeds.

The invention claimed is:

1. A compound of formula I:

I

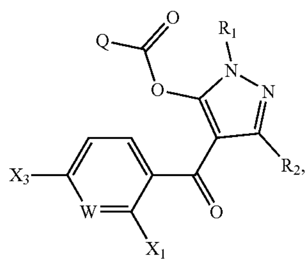

wherein:

$X_1$ is methyl or chloro;

W is $CX_2$;

$X_2$ is $Y_1$ oxy;

$Y_1$ is $C_1$-$C_6$ alkyl, $C_1$-$C_6$ haloalkyl, $C_3$-$C_6$ cycloalkyl, or $C_3$-$C_6$ cycloalkyl $C_1$-$C_6$ alkyl;

$X_3$ is methylsulfonyl;

Q is $Q_1$ or $Q_3$ $Q_1$

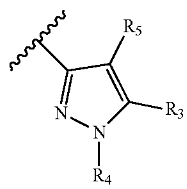

$Q_3$

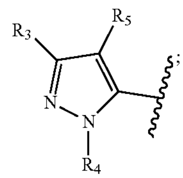

$R_1$ is $C_1$-$C_6$ haloalkyl, $C_3$-$C_6$ cycloalkyl $C_1$-$C_3$ alkyl, or $C_1$-$C_6$ alkoxy $C_1$-$C_3$ alkyl;

$R_2$ and $R_3$ are the same or different, and are independently selected from hydrogen, $C_1$-$C_6$ haloalkyl, $C_3$-$C_6$ cycloalkyl, and $C_3$-$C_6$ cycloalkyl $C_1$-$C_6$ alkyl;

$R_4$ is ethyl; and $R_5$ is hydrogen or halogen.

2. A compound of formula I:

I

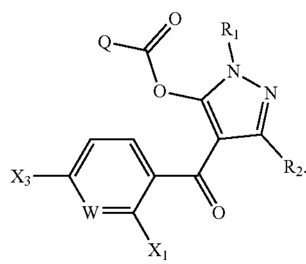

wherein:

$X_1$ is methyl or chloro;

W is $CX_2$;

$X_2$ is $Y_1$ oxy;

$Y_1$ is $C_1$-$C_6$ alkyl, $C_3$-$C_6$ cycloalkyl $C_1$-$C_6$ alkyl, or $C_1$-$C_6$ alkoxy $C_1$-$C_6$ alkyl;

$X_3$ is methylsulfonyl;

Q is selected from $Q_1$ or $Q_3$:

$Q_1$

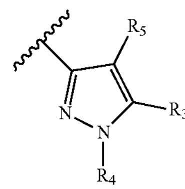

$Q_3$

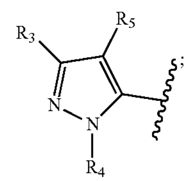

$R_1$ is $C_1$-$C_6$ alkyl;

$R_2$ and $R_3$ are the same or different, and are independently selected from hydrogen, $C_1$-$C_6$ alkyl, and $C_3$-$C_6$ cycloalkyl;

$R_4$ is ethyl; and $R_5$ is hydrogen.

3. A herbicidal composition, comprising an active ingredient and an agriculturally acceptable carrier, wherein the active ingredient is the compound of the formula I according to claim 1, and a weight percentage of the active ingredient in the composition is 1-99%.

4. A method for controlling weeds, comprising applying a herbicidally effective dose of the herbicidal composition of claim 3 to a weed or a growth medium or site of the weed.

5. A herbicidal composition, comprising an active ingredient and an agriculturally acceptable carrier, wherein the active ingredient is the compound of the formula I according to claim 2, and a weight percentage of the active ingredient in the composition is 1-99%.

6. A method for controlling weeds, comprising applying a herbicidally effective dose of the herbicidal composition of claim 5 to a weed or a growth medium or site of the weed.

* * * * *